(12) United States Patent
Faulhaber et al.

(10) Patent No.: US 11,666,454 B2
(45) Date of Patent: Jun. 6, 2023

(54) SURGICAL PLATE SYSTEMS

(71) Applicant: GLOBUS MEDICAL, INC., Audubon, PA (US)

(72) Inventors: Kurt Faulhaber, Renton, WA (US); Bala Sundararajan, Exton, PA (US)

(73) Assignee: Globus Medical, Inc., Audubon, PA (US)

( * ) Notice: Subject to any disclaimer, the term of this patent is extended or adjusted under 35 U.S.C. 154(b) by 316 days.

(21) Appl. No.: 17/028,501

(22) Filed: Sep. 22, 2020

(65) Prior Publication Data

US 2021/0007859 A1 Jan. 14, 2021

Related U.S. Application Data

(63) Continuation of application No. 15/444,512, filed on Feb. 28, 2017, now Pat. No. 10,786,365, which is a continuation of application No. 14/664,291, filed on Mar. 20, 2015, now Pat. No. 9,615,931.

(51) Int. Cl.
*A61F 2/44* (2006.01)
*A61B 17/70* (2006.01)
*A61B 17/80* (2006.01)
*A61F 2/30* (2006.01)

(52) U.S. Cl.
CPC .......... *A61F 2/447* (2013.01); *A61B 17/7059* (2013.01); *A61B 17/8047* (2013.01); *A61F 2/30771* (2013.01); *A61F 2/44* (2013.01); *A61F 2/442* (2013.01); *A61F 2/4455* (2013.01); *A61F 2002/30266* (2013.01); *A61F 2002/30593* (2013.01); *A61F 2002/30774* (2013.01); *A61F 2002/30785* (2013.01); *A61F 2002/30787* (2013.01); *A61F 2002/30843* (2013.01); *A61F 2002/30904* (2013.01); *A61F 2002/449* (2013.01); *A61F 2002/4415* (2013.01); *A61F 2002/4435* (2013.01)

(58) Field of Classification Search
CPC ...... A61B 17/80; A61B 17/8004–8014; A61B 17/809; A61B 17/8028; A61B 17/8061; A61B 17/8095; A61B 17/58; A61B 17/68; A61B 17/70; A61B 17/7044; A61B 17/7059; A61B 2017/681; A61F 2/44; A61F 2/4455; A61F 2/446; A61F 2/4465; A61F 2/447; A61F 2002/449
See application file for complete search history.

(56) References Cited

U.S. PATENT DOCUMENTS

| | | | |
|---|---|---|---|
| 5,269,784 A | * | 12/1993 | Mast ..................... A61B 17/60 606/288 |
| 6,682,563 B2 | | 1/2004 | Scharf |
| 7,112,222 B2 | | 9/2006 | Fraser et al. |
| 8,690,928 B1 | | 4/2014 | Walkenhorst et al. |

(Continued)

*Primary Examiner* — Eduardo C Robert
*Assistant Examiner* — Michelle C Eckman

(57) ABSTRACT

Improved bone plate systems are described herein. In some instances, a bone plate system can include a base plate, at least one retainer plate, and at least one spacer. The at least one retainer plate is configured to reside on the base plate in a free floating manner and can receive at least one fastener to secure the retainer plate to the at least one spacer, thereby providing a plate system that attaches to a spacer. In other instances, a bone plate system can include a base plate having one or more push plates that can engage at least one spacer.

9 Claims, 27 Drawing Sheets

(56) References Cited

U.S. PATENT DOCUMENTS

| | | | |
|---|---|---|---|
| 2005/0101960 A1* | 5/2005 | Fiere | A61F 2/4611 |
| | | | 623/17.11 |
| 2012/0041559 A1* | 2/2012 | Melkent | A61F 2/4611 |
| | | | 623/17.11 |
| 2012/0172987 A1 | 7/2012 | Phillips et al. | |
| 2012/0184959 A1* | 7/2012 | Price | A61B 17/8095 |
| | | | 606/70 |
| 2013/0268080 A1 | 10/2013 | Melkent et al. | |
| 2014/0058446 A1* | 2/2014 | Bernstein | A61B 50/20 |
| | | | 606/246 |
| 2014/0204712 A1* | 7/2014 | Skinner | E21B 47/135 |
| | | | 367/81 |

\* cited by examiner

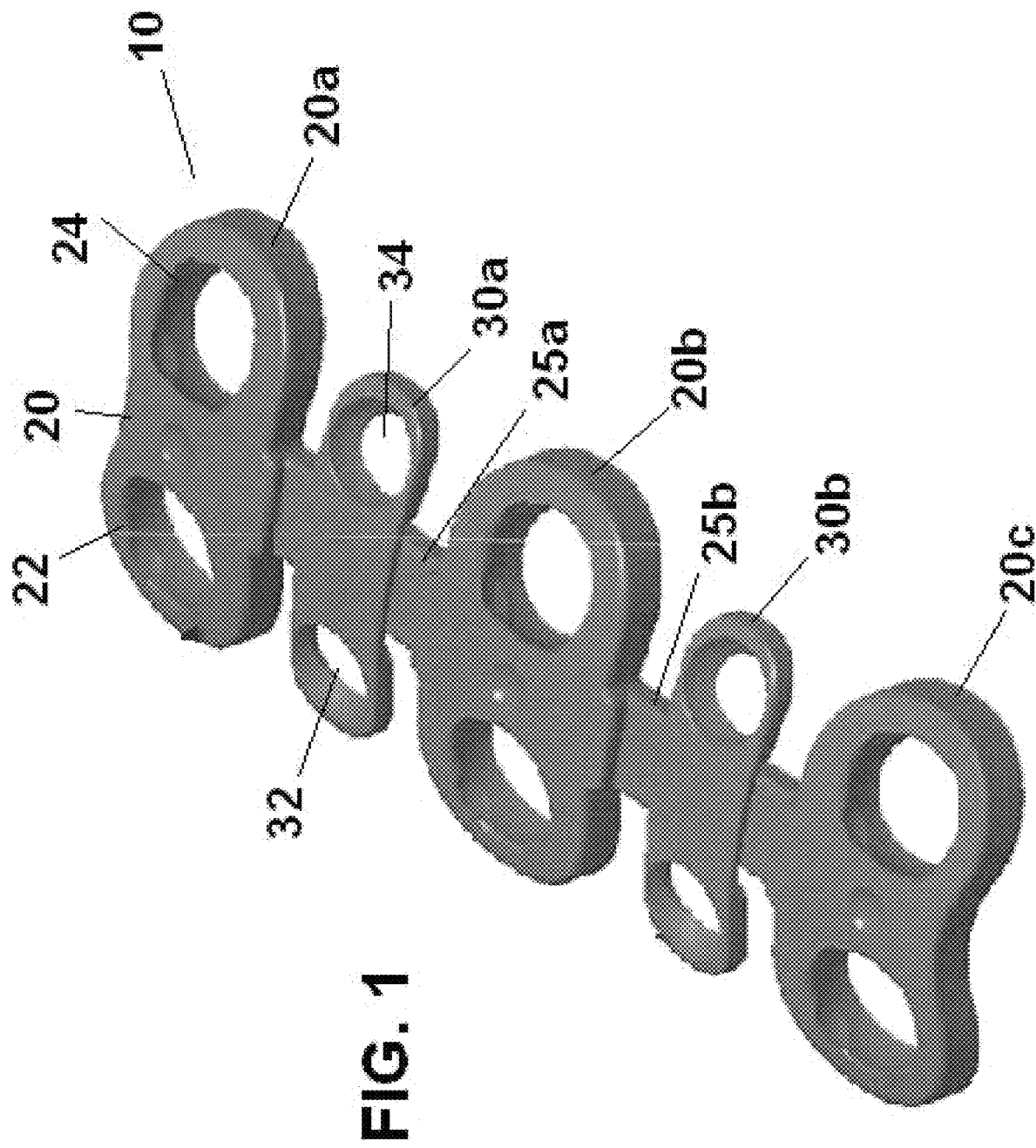

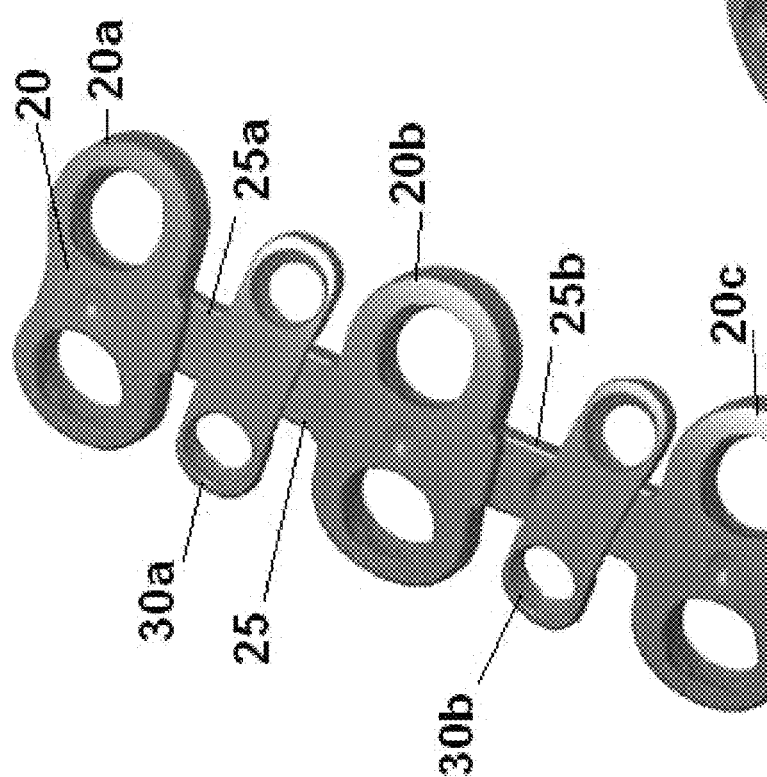
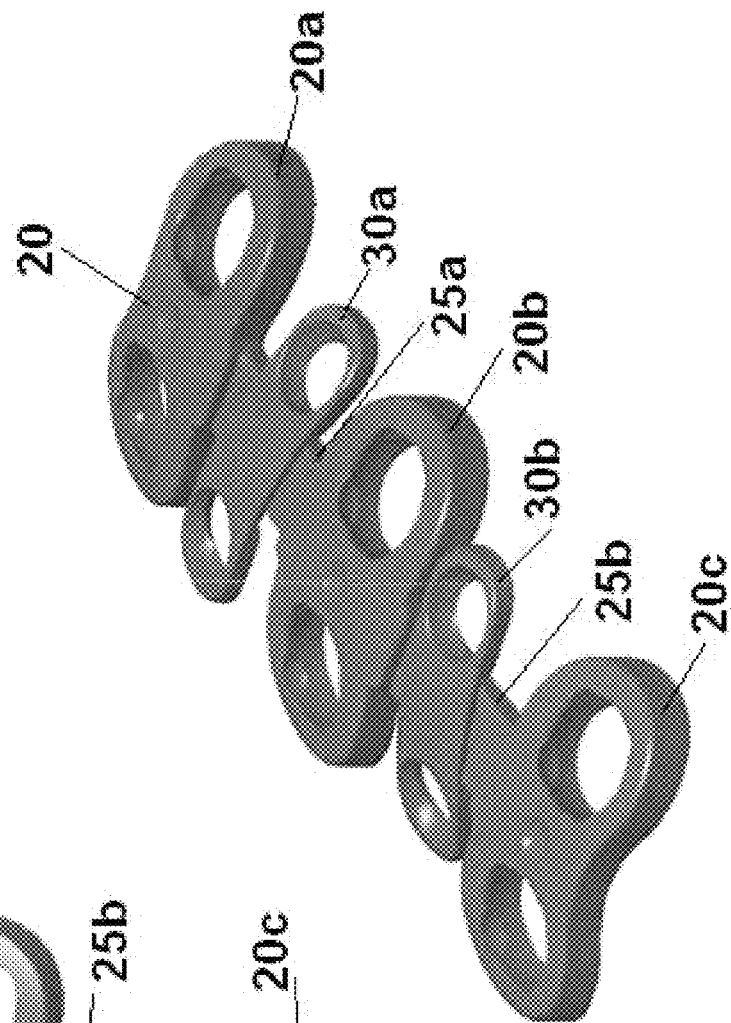
FIG. 3A
FIG. 3B

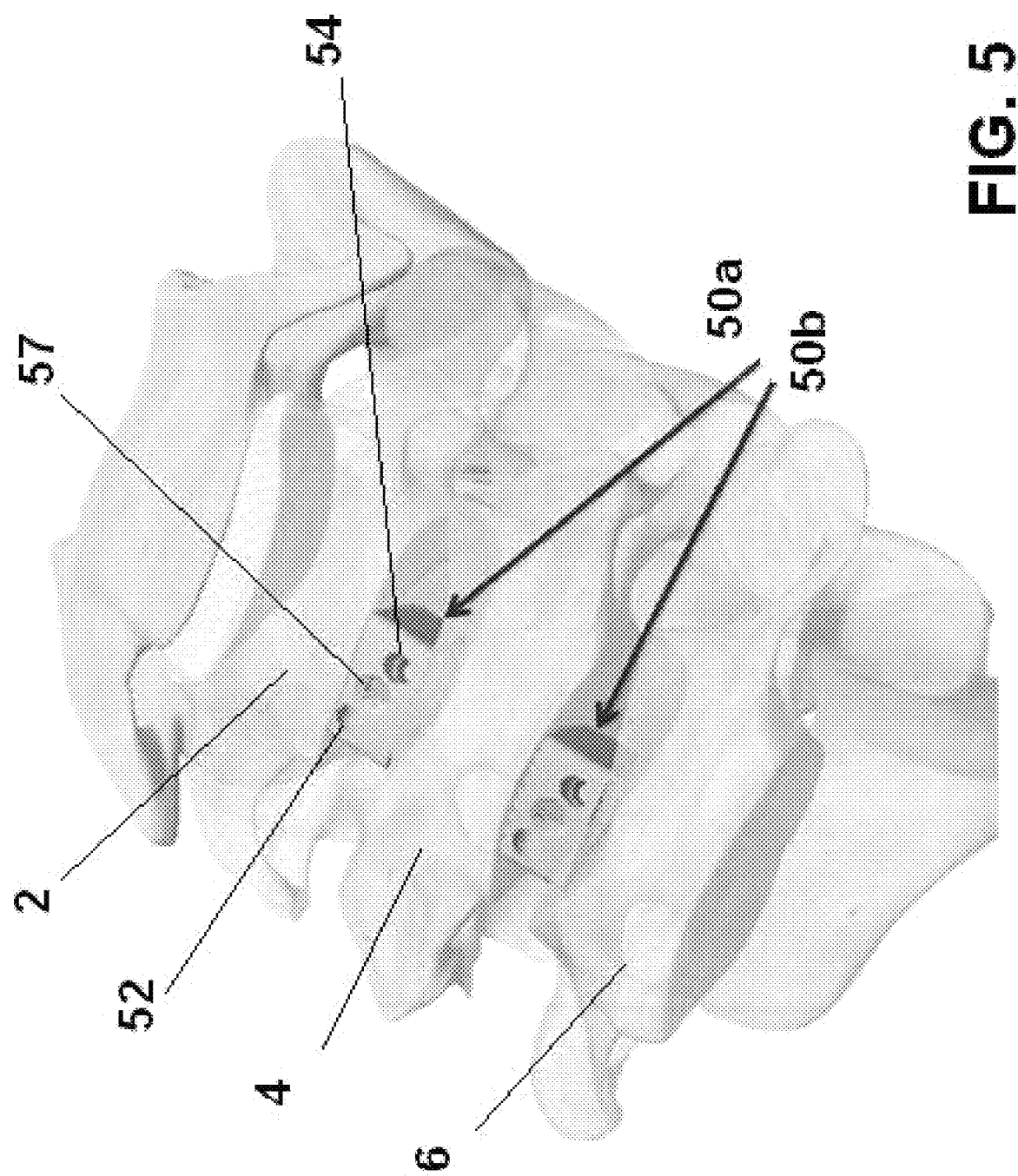

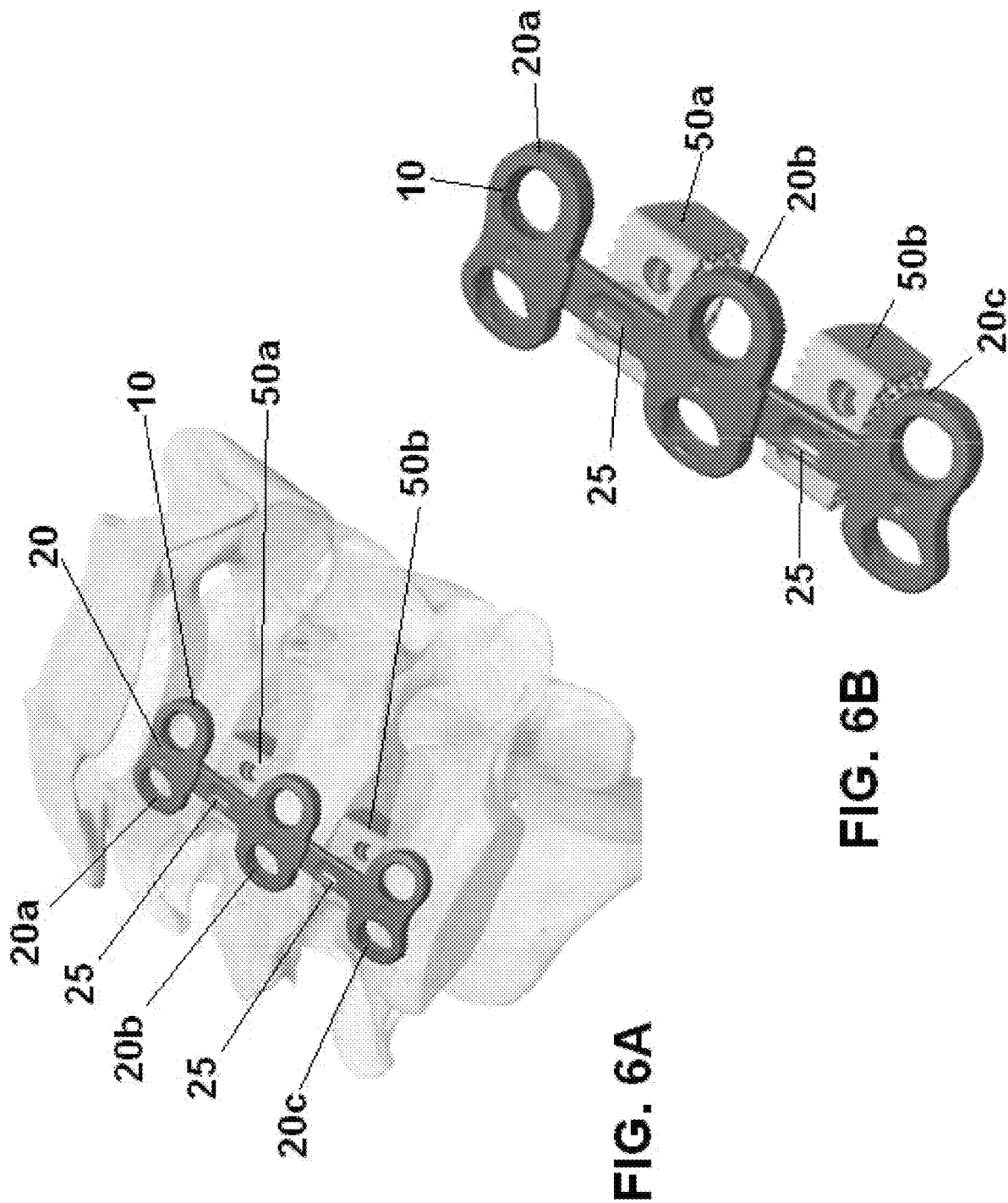

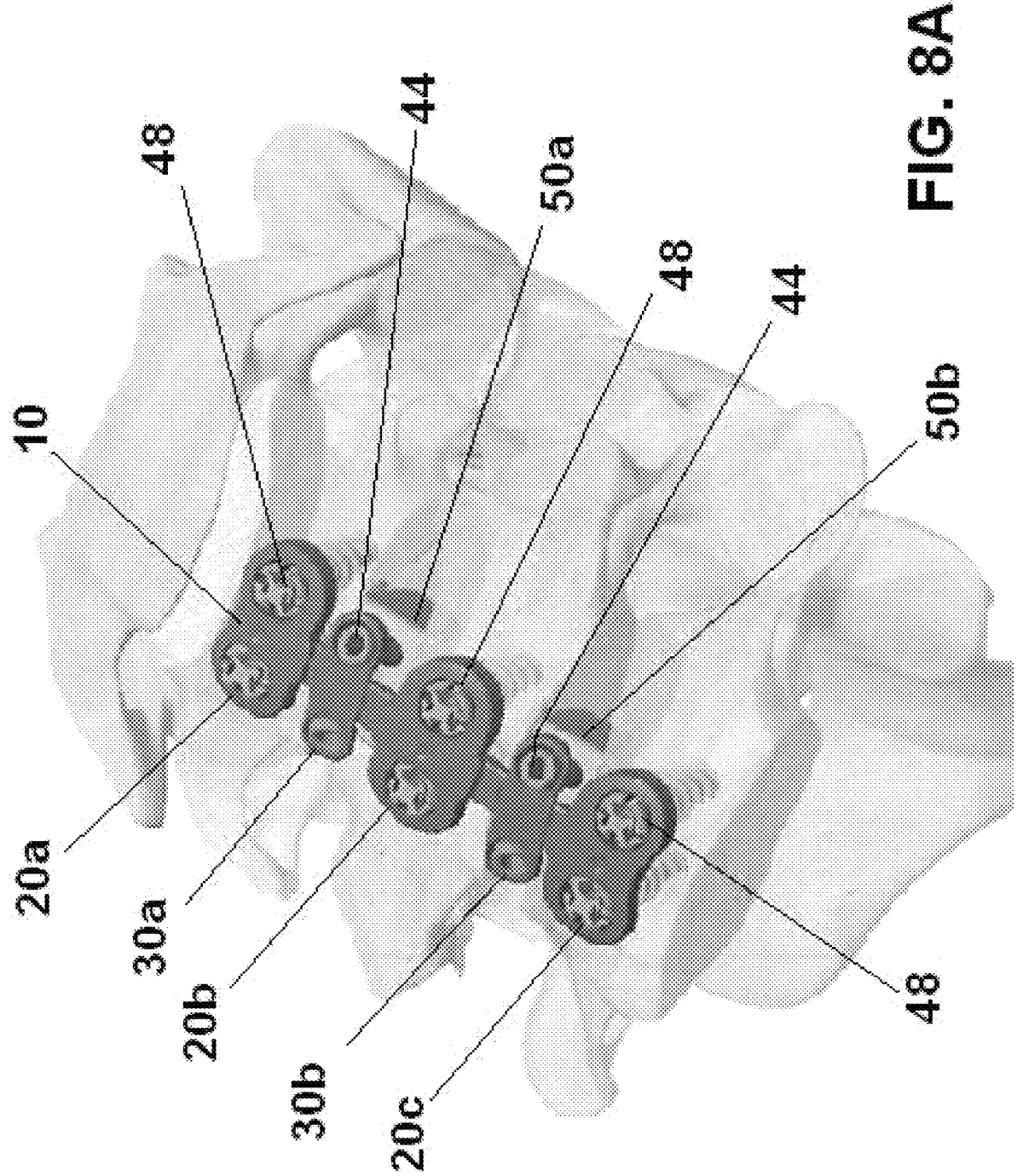

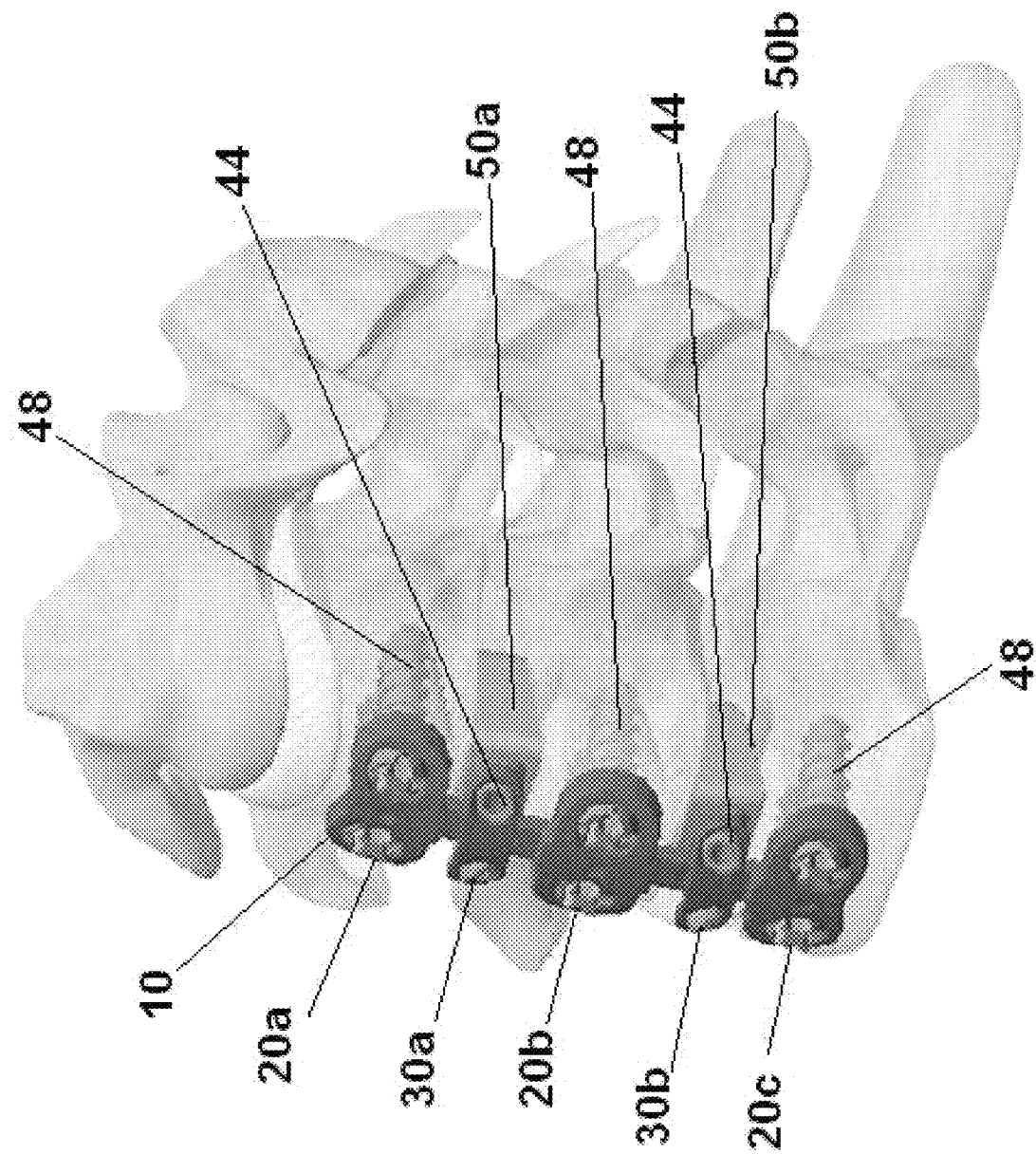

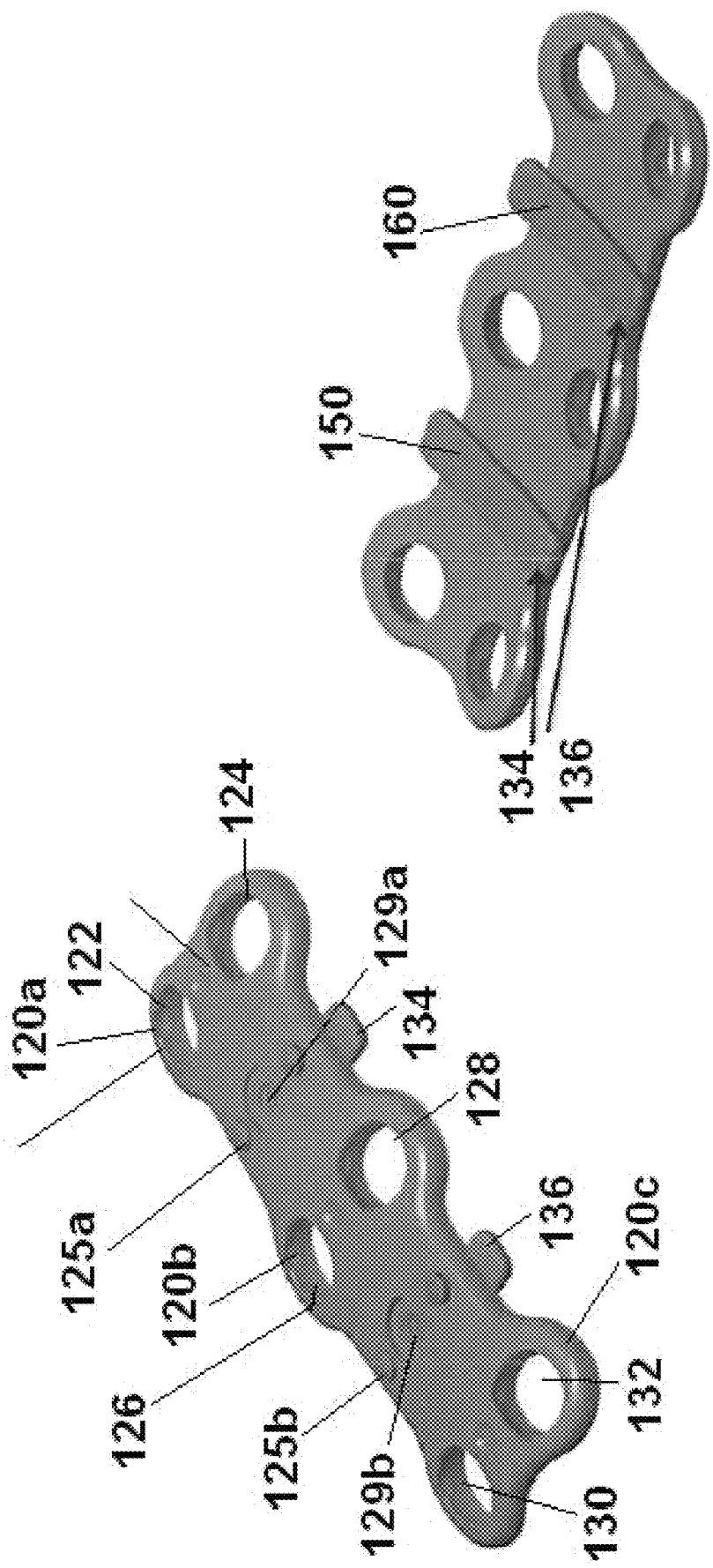

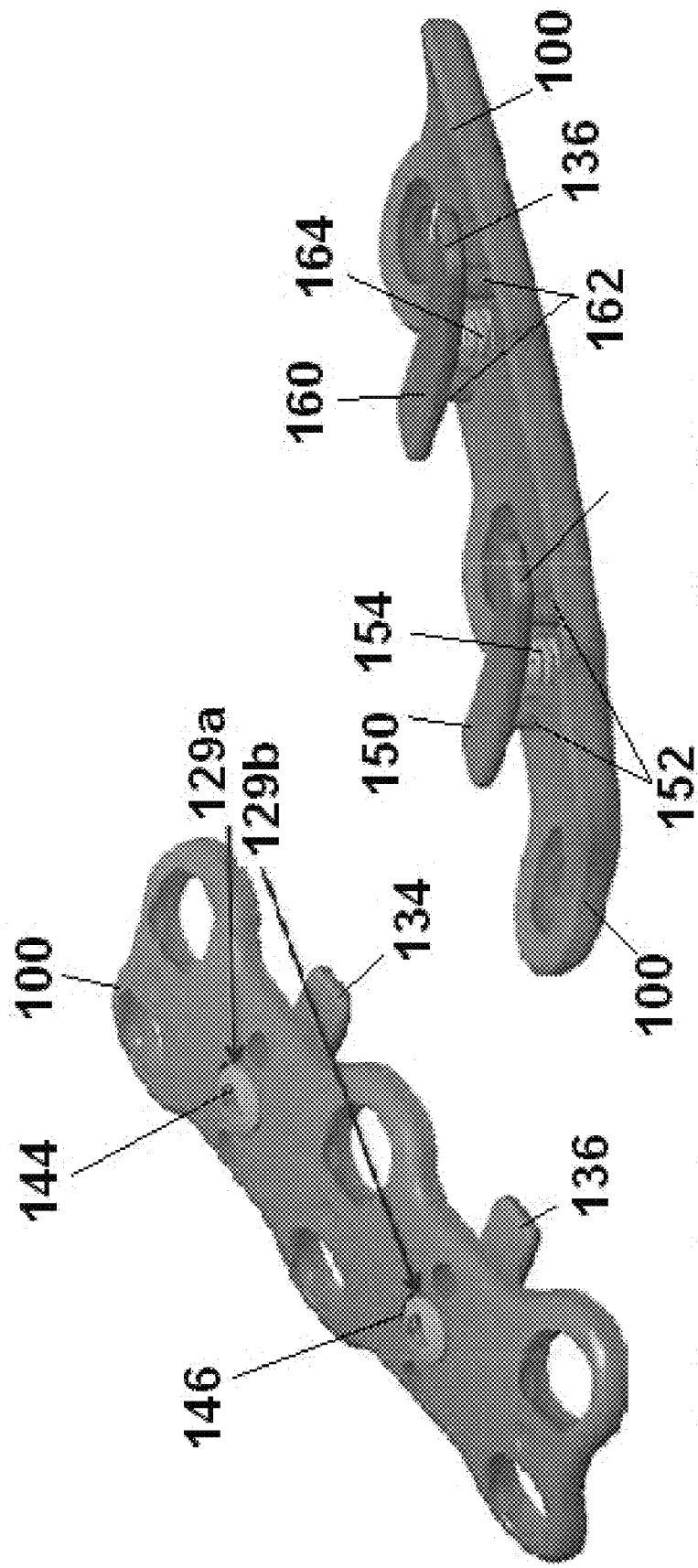

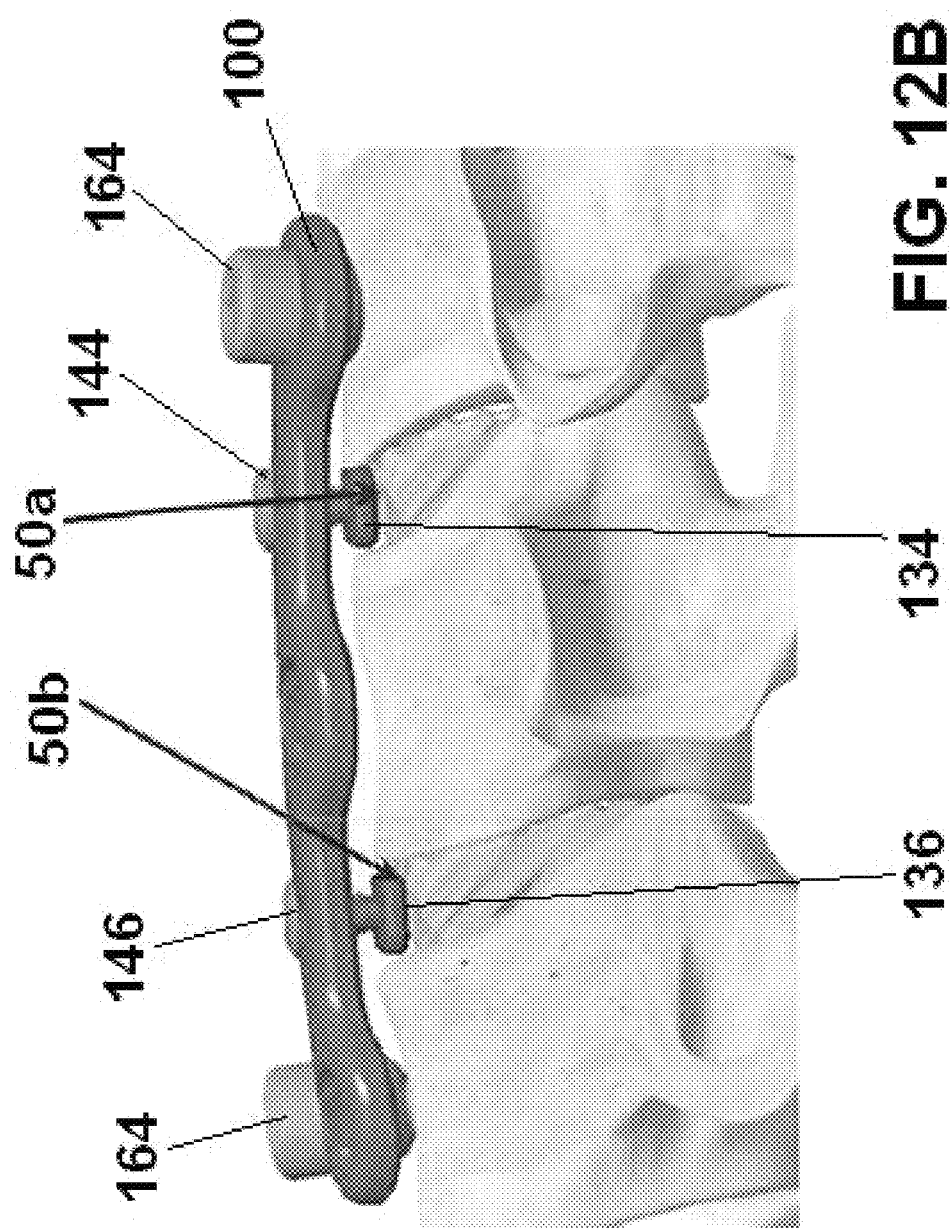

SURGICAL PLATE SYSTEMS

CROSS REFERENCE TO RELATED APPLICATIONS

The present application is a continuation of U.S. application Ser. No. 15/444,512 filed on Feb. 28, 2017, which is a continuation of U.S. application Ser. No. 14/664,291 filed on Mar. 20, 2015, all of which are incorporated in their entirety herein.

FIELD OF THE INVENTION

The present application relates to improved surgical plate systems, particularly those used with the spine.

BACKGROUND OF THE INVENTION

Millions are affected by back and neck pain. Many patients can respond well to non-surgical treatments. However, many others may turn to surgical solutions to alleviate their pain. In some instances, the pain can be caused from a herniated disc. A disc herniates when some of the disc's gel like center bulges or ruptures through the outer ring of the disc and presses on nerve roots or the spinal cord. To alleviate the pain, a surgeon may perform a procedure called a discectomy and fusion, whereby the disc is removed and a replacement disc with bone graft is inserted therein. A plate can then be screwed into adjacent vertebral bones, thereby stabilizing the spine and facilitating fusion and healing. There is a constant need for improved plate and plate systems that can be used in surgical procedures.

SUMMARY OF THE INVENTION

Embodiments of the present application include the following. In some embodiments, an implantable system comprises a first spacer, a second spacer, and a plate system configured to engage the first spacer and the second spacer, wherein the plate system comprises: a base plate comprising an upper portion, a mid portion and a lower portion; a first bridge positioned between the upper portion and the mid portion; a second bridge positioned between the mid portion and the lower portion; a first retainer plate in engagement with the first bridge; and a second retainer plate in engagement with the second bridge, wherein the first retainer plate is configured to receive a first pair of fasteners for extending into the first spacer; wherein the second retainer plate is configured to receive a second pair of fasteners for extending into the second spacer.

In other embodiments, an implantable system comprises a first spacer; a second spacer; a plate system attachable to the first spacer and the second spacer, wherein the plate system comprises: a base plate; a first retainer plate in contact with the base plate, wherein the first retainer plate is configured to receive at least one fastener that extends into the first spacer; and a second retainer plate in contact with the base plate, wherein the second retainer plate is configured to receive at least one fastener that extends into the second spacer.

In other embodiments, an implantable system comprises: a first spacer; a second spacer; a plate system attachable to the first spacer and the second spacer, wherein the plate system comprises: a base plate; a first retainer plate configured to receive at least one fastener that extends into the first spacer; and a second retainer plate configured to receive at least one fastener that extends into the second spacer.

BRIEF DESCRIPTION OF THE DRAWINGS

The application will be more readily understood with reference to the embodiments thereof illustrated in the attached figures, in which:

FIG. 1 is a top perspective view of an improved plate system including a base plate and one or more retainer plates in accordance with some embodiments;

FIGS. 3A and 3B are different views of the improved plate system in FIG. 1, whereby a base plate is engaged with one or more retainer plates;

FIG. 5 is a perspective view of one or more spacers inserted in between vertebrae in accordance with some embodiments;

FIGS. 6A and 6B are different views of a base plate overlying the one or more spacers in FIG. 5 in accordance with some embodiments;

FIGS. 8A-8C are different views of the improved plate system and associated spacers in a final construct in accordance with some embodiments;

FIGS. 9A and 9B are different views of an alternative improved plate system including a base plate and one or more push plates in accordance with some embodiments;

FIGS. 10A and 10B are different views of the improved plate system shown in FIGS. 9A and 9B in accordance with some embodiments;

FIGS. 12A and 12B are different views of the improved plate system shown in FIGS. 11A and 11B with the push plates pushed outwardly to the spacers in a second configuration in accordance with some embodiments;

DETAILED DESCRIPTION OF THE ILLUSTRATED EMBODIMENTS

Embodiments of the application will now be described. The following detailed description of the application is not intended to be illustrative of all embodiments. In describing embodiments of the present application, specific terminology is employed for the sake of clarity. However, the application is not intended to be limited to the specific terminology so selected.

The present application is directed to improved plate systems, devices and methods. The plate systems are used with spacers in fusion procedures. As discussed further below, the plate systems provide a number of advantages, such as providing less stress on spacers and the spine in general. While the improved plate systems, devices and methods can be used in any part of the spine, including the lumbar and thoracic regions, the systems can be used particularly in the cervical region.

FIGS. 1-8C relate to embodiments of a plate system including one or more retainer plates that can be operably attached or connected to an implanted spacer. In some surgical procedures, implanted spacers can migrate within a disc space. The unintended migration of the spacers causes stress to increase on both the spacer and the spine in general. The plate system embodiments shown in FIGS. 1-8C are designed to alleviate spacer migration by providing one or more retainer plates capable of attachment to one or more spacers, thereby fixing the one or more spacers to the plate system and adjacent vertebral bodies.

Figure 7A:
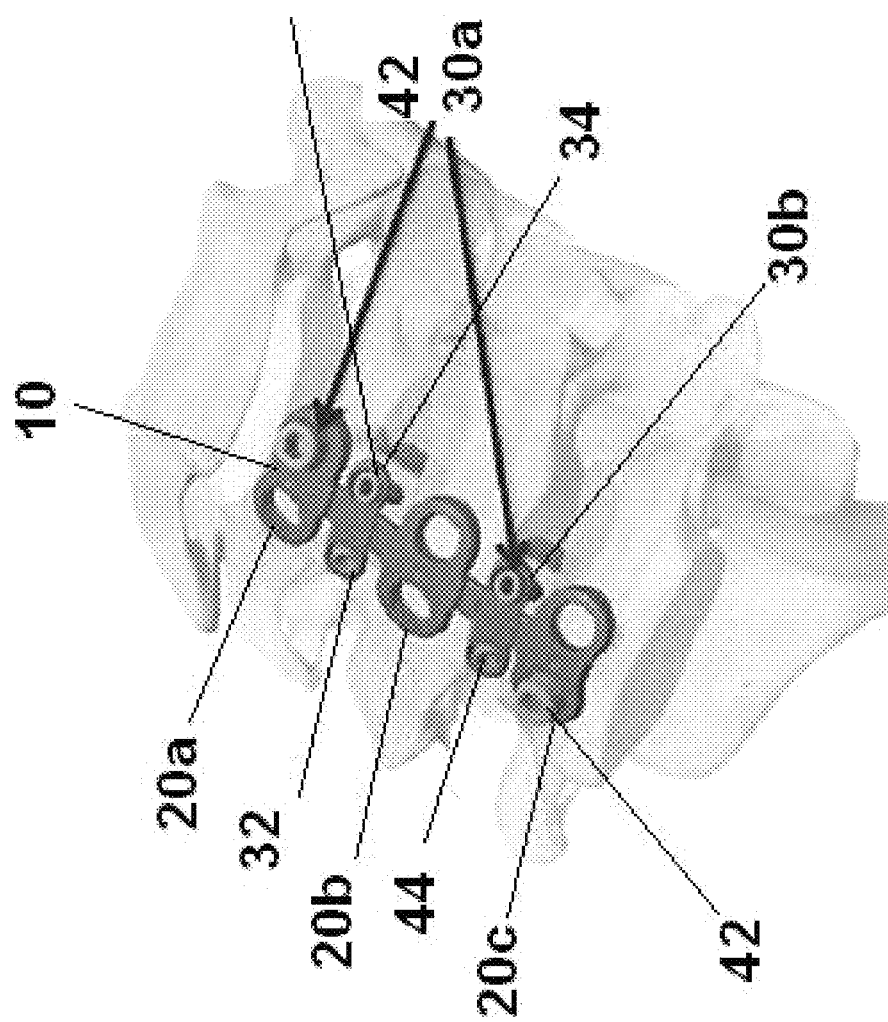
FIGS. 7A-7C are different views of the base plate and retainer plates overlying the one or more spacers in FIG. 5 in accordance with some embodiments.
Figure 7C:
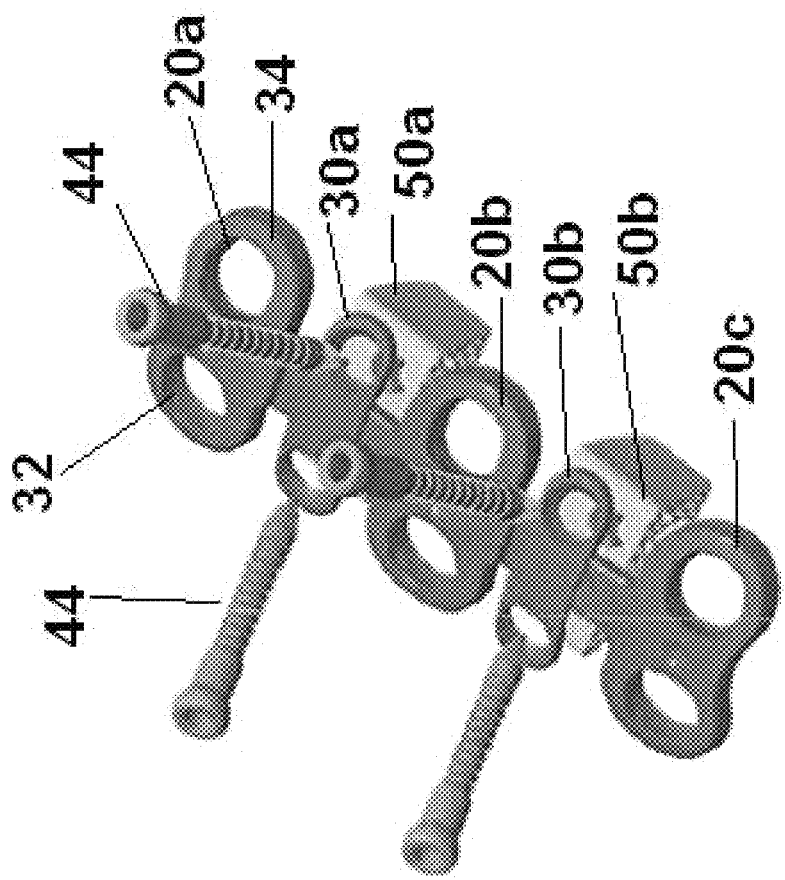
Figure 7B:
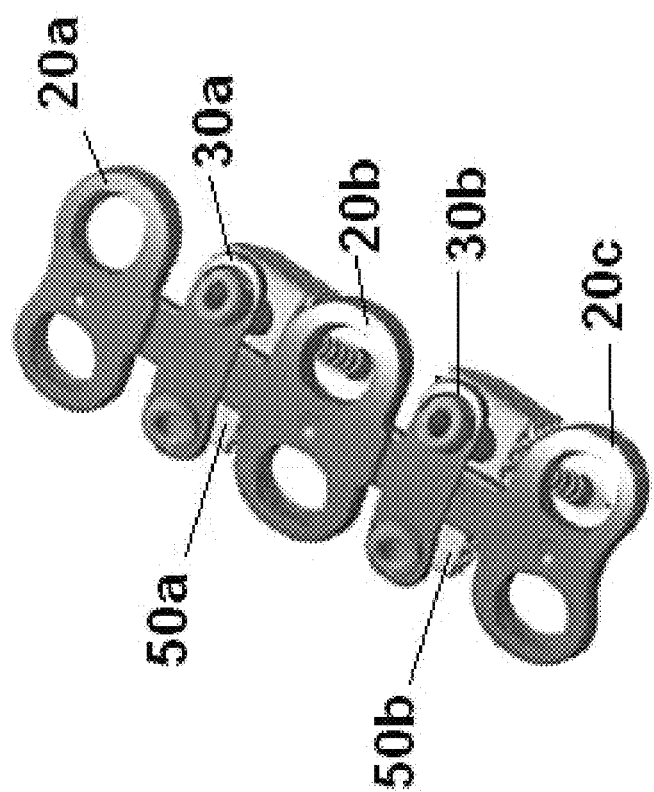

FIG. 1 is a top perspective view of an improved plate system including a base plate and one or more retainer plates in accordance with some embodiments. In some embodiments, the one or more retainer plates 30a and 30b are capable of attaching to the base plate 20. The one or more retainer plates 30a and 30b are advantageously capable of being secured to one or more spacers (as shown in FIGS. 7A-7C), thereby reducing the risk of spacer migration within the disc space.

In some embodiments, the plate system 10 comprises a base plate 20 including an upper portion 20a, a mid portion 20b and a lower portion 20c. Each of the upper portion 20a, mid portion 20b and lower portion 20c of the base plate 20 comprise a first opening 22 and a second opening 24 for receiving one or more fasteners. The one or more fasteners can include screws (either temporary or permanent) that are inserted into vertebral bone. While the present embodiment illustrates a pair of openings 22, 24 on each of the portions 20a, 20b, 20c of the base plate 20, in other embodiments, each of the portions can include a single elongated opening (either circular or elongated) or more than two openings for receiving additional screws for fixation into bone. In some embodiments, the upper portion 20a of the base plate 20 can be attached to a first vertebral body, the mid portion 20b of the base plate 20 can be attached to a second vertebral body, and the lower portion 20c can be attached to a third vertebral body. The upper portion 20a can be connected to the mid portion 20b via a first bridge 25a, while the mid portion 20b can be connected to the lower portion 20c via a second bridge 25a.

Each of the upper portion 20a, mid portion 20b and lower portion 20c of the base plate 20 includes rounded surfaces to advantageously reduce damage to surrounding tissue that abut the base plate 20. In some embodiments, each portion 20a, 20b and 20c has completely edgeless surfaces. In some embodiments, the upper portion 20a, mid portion 20b and lower portion 20c of the base plate 20 are flat, such that each of their upper surface is parallel to a lower surface. In other embodiments, the upper portion 20a, mid portion 20b and lower portion 20c of the base plate 20 can be curved and possibly convexly shaped. By having a curvature, each of the upper portion 20a, mid portion 20b and lower portion 20c of the base plate 20 can easily conform to bone that is positioned beneath the base plate 20.

As shown in FIG. 1, one or more retainer plates can reside over the base plate in accordance with some embodiments. In some embodiments, a first retainer plate 30a is positioned over the first bridge 25a between the upper portion 20a and the mid portion 20b of the base plate, while the second retainer plate 30b is positioned over the second bridge 25b between the mid portion 20b and the lower portion 20c of the base plate. Each of the first retainer plate 30a and the second retainer plate 30b includes a first opening 32 and a second opening 34 for receiving one or more fasteners. The one or more fasteners can include screws (temporary or permanent) that are inserted into a spacer body. While the present embodiment illustrates a pair of openings 32, 34 formed through each of the retainer plates 30a, 30b, in other embodiments, each of the retainer plates can include a single elongated opening (either circular or elongated) or more than two openings for receiving additional screws for fixation into a spacer.

Each of the first retainer plate 30a and the second retainer plate 30b includes rounded surfaces to advantageously reduce damage to surrounding tissue that abut the retainer plates. In some embodiments, each retainer plate 30a, 30b has completely edgeless surfaces. In some embodiments, the retainer plates 30a, 30b are flat, such that each of their upper surface is parallel to a lower surface. In other embodiments, the retainer plates 30a, 30b can be curved and possibly convexly shaped. By having a curvature, each of the retainer plates 30a, 30b can conform to the underlying based plate 20, which may also have some curvature. Furthermore, by having curvature, each of the retainer plates 30a, 30b can be brought closer to a spacer to which they are attached.

In some embodiments, both the base plate 20 and the retainer plates 30a, 30b can be formed of a metal. In some embodiments, the base plate 20 is formed of a same metal as the retainer plates 30a, 30b. In other embodiments, the base plate 20 is formed of a different metal as the retainer plates 30a, 30b. In some embodiments, at least one of the base plate 20 and the retainer plates 30a, 30b is formed of titanium or a titanium alloy. Other possible metals for use include vanadium, aluminum, steel, cobalt and their alloys.

Figure 2B:
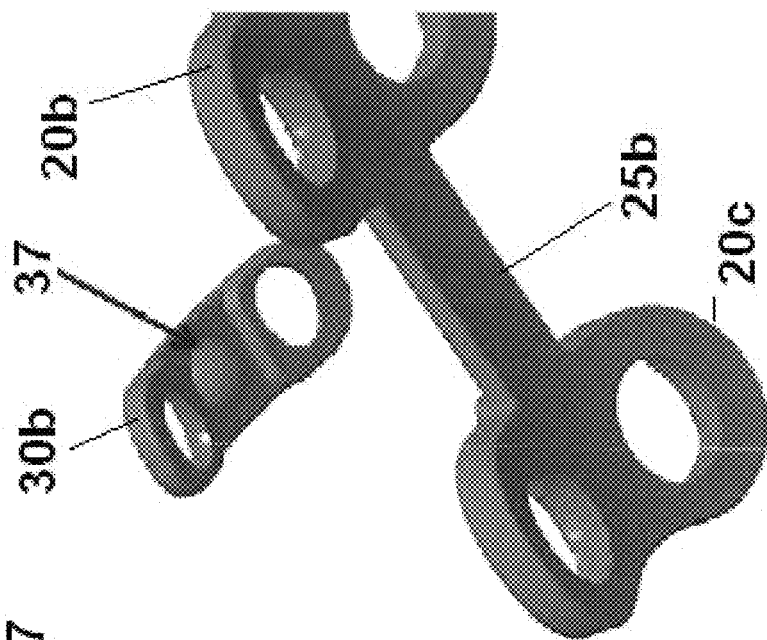
FIGS. 2A and 2B are different views of the improved plate system in FIG. 1 whereby a base plate is shown separated from a retainer plate.
Figure 2A:
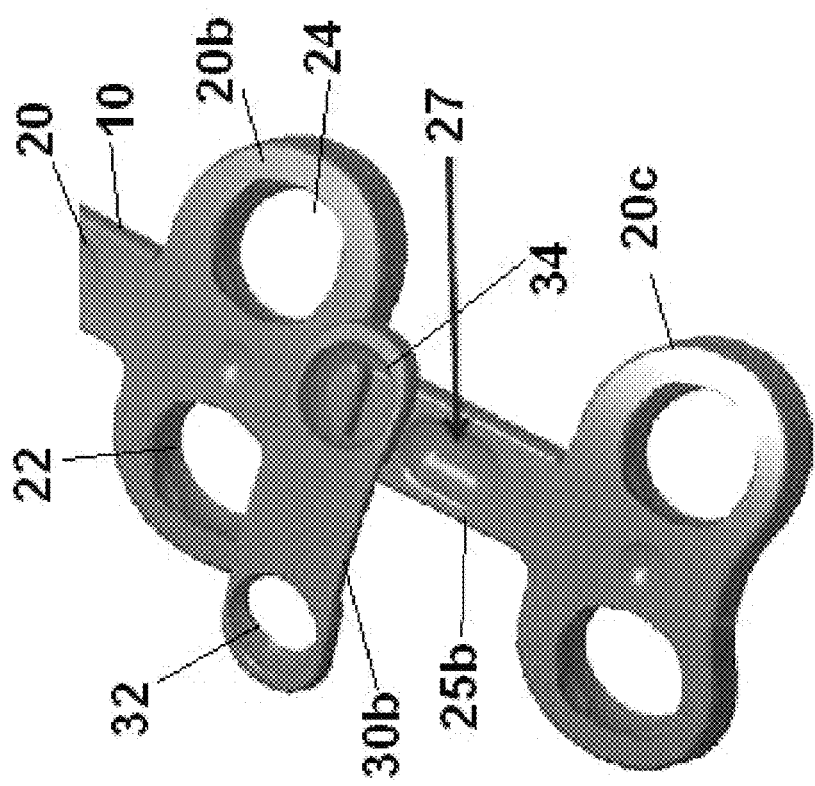

FIGS. 2A and 2B are different views of the improved plate system in FIG. 1 whereby a base plate is shown separated from a retainer plate. FIG. 2A illustrates a top view of the retainer plate 30b, while FIG. 2B illustrates a bottom view of the retainer plate 30b.

The retainer plate 30b is independent and separate from the base plate 20. As shown in FIG. 2A, the base plate 20 can include an engagement feature 27 positioned in the bridge 25b in the form of a channel, opening or recess. In some embodiments, the engagement feature 27 comprises a circular, oval or otherwise rounded channel. The engagement feature 27 is designed to receive a bump out portion 37 (shown in FIG. 2B) that extends from a bottom of the retainer plate 30b. In some embodiments, the bump out portion 37 is similarly circular, oval or otherwise rounded, such that it can be easily received in the engagement feature 27. Accordingly, the retainer plate 30b easily engages the base plate 20 via the bump out portion 37.

FIGS. 3A and 3B are different views of the improved plate system in FIG. 1, whereby a base plate is engaged with one or more retainer plates. In some embodiments, the plate 20 is engaged by at least two retainer plates 30a and 30b. The retainer plates 30a, 30b each include bump out portions 37 (as shown in FIG. 2B) that are received in respective engagement features 27 positioned on the first bridge 25a and the second bridge 25b.

When the retainer plates 30a, 30b are engaged with the base 20, the retainer plates 30a, 30b remain generally free floating with the base 20 such that they can still have dynamic motion relative to the base 20. This dynamic motion is allowed by the interface between the bump out 37 of the retainer plates 30a, 30b and the engagement features 27 of the base 20, which can all be for example, spherical. As shown in FIG. 3A, the retainer plate 30b can be slightly angled, such that it can be offset from an axis that is perpendicular to the longitudinal axis of the base 20. The advantage of having the retainer plates 30a, 30b maintain dynamic motion relative to the base 20 is that the retainer plates 30a, 30b can be placed at any number of angles that allows them to more easily attach to particular spacers that could be oriented differently in the body.

In some embodiments, the retainer plates 30a, 30b remain free floating with respect to the base 20 such that they can be easily removed from the retainer plates 30a, 30b. In the free floating configuration, the retainer plates 30a, 30b have little if any securing to the base 20. In some embodiments, the retainer plates 30a, 30b remain free floating relative to the base 20 until the retainer plates 30a, 30b are secured to corresponding spacers. In other embodiments, the retainer plates 30a, 30b can be attached to the base 20. For example, in some embodiments, the engagement between the retainer plates 30a, 30b and the base 20 can be a friction fit, such as a snap fit, that secures the different components together. Even under these circumstances, the retainer plates 30a, 30b may be capable of dynamic motion relative to the base 20, based on the shape of corresponding bump outs 37 and engagement features 27.

FIGS. 4A-4E are different views of a spacer for use with a plate system in accordance with some embodiments. The spacer 50 comprises an upper surface 52 for engaging an upper vertebral body and a lower surface 54 for engaging a lower vertebral body. Each of the upper surface 52 and the lower surface 54 comprise protrusions, teeth or ribbing that help to engage bone. An opening 53 extends from the upper surface 52 to the lower surface 54 of the spacer 50. The opening 53 is configured to receive graft material therein. In some embodiments, the spacer 50 can be packed with graft material before being inserted into a disc space. In other embodiments, the spacer 50 can be packed with graft material after being inserted into a disc space.

Figure 4A:
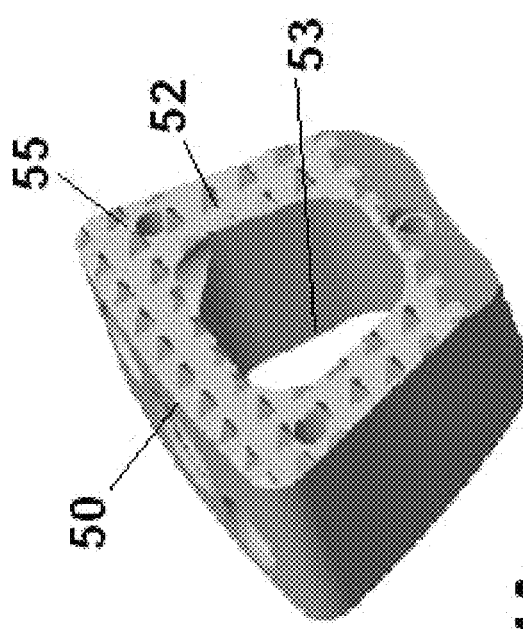
FIGS. 4A-4E are different views of a spacer in accordance with some embodiments.
Figure 4B:
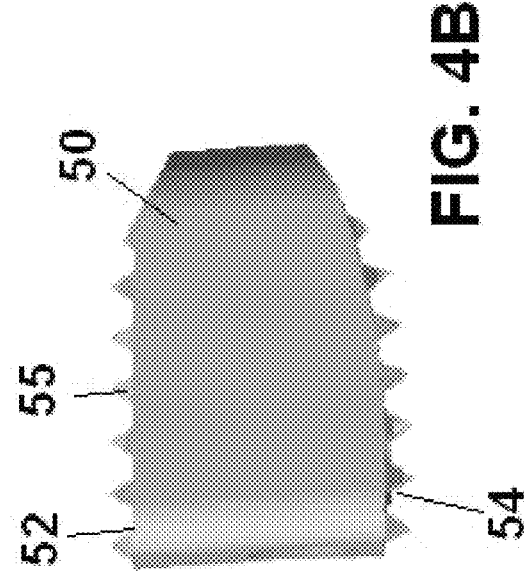
Figure 4C:
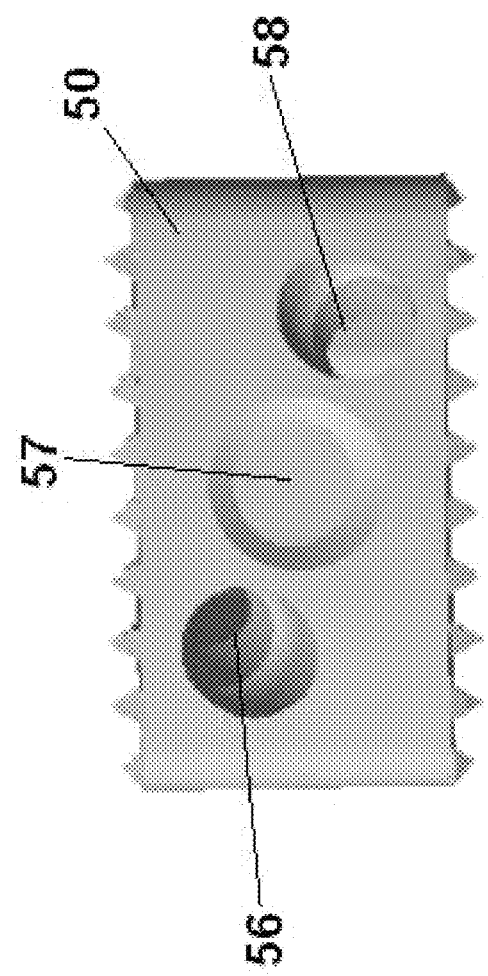
Figure 4D:
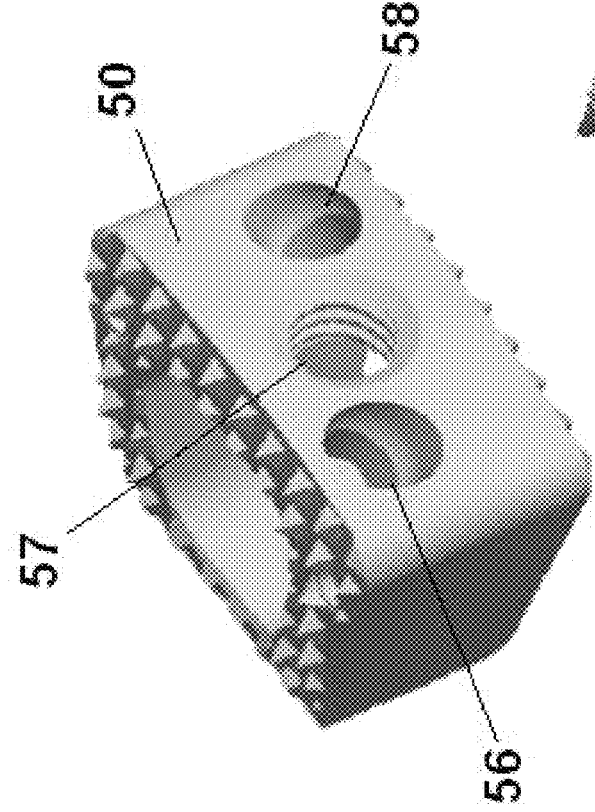
Figure 4E:
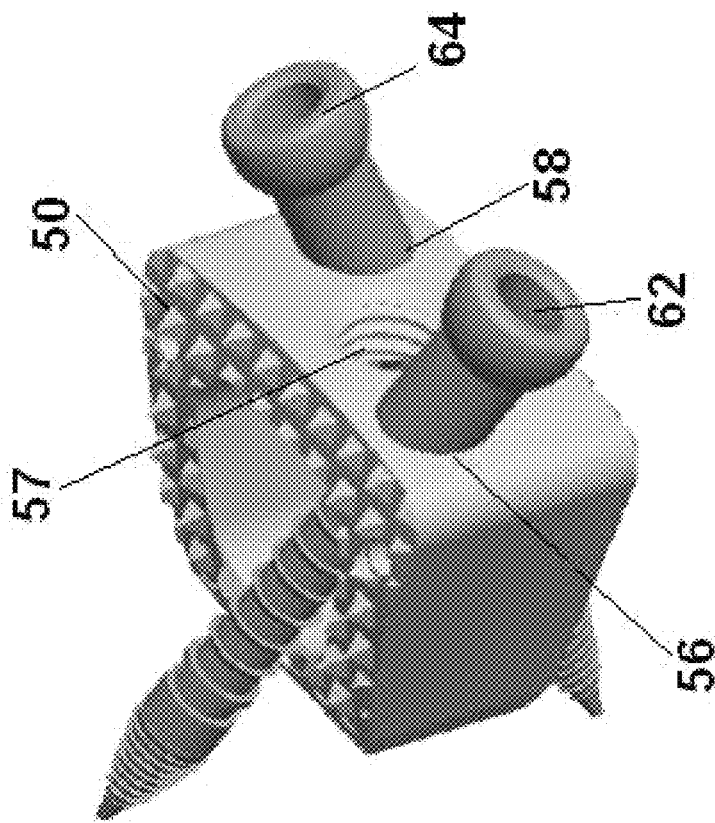

The spacer 50 comprises a leading end and a trailing end. As shown in FIG. 4B, in some embodiments, the leading end can be chamfered or tapered to assist in distraction of bone. FIG. 4C shows a view of the trailing end of the spacer 50. From this view, one can see a first screw opening 56, a second screw opening 58 and a tool opening 57 positioned therebetween. The first screw opening 56 is configured to receive a first fastener 62, while the second screw opening 58 is configured to receive a second fastener 64 (as shown in FIG. 4E). In some embodiments, the first fastener 62 is configured to extend initially through a first opening 22 in a retainer plate before passing through the first screw opening 56 in the spacer 50, thereby helping to secure the plate 10 to the spacer 50. Likewise, the second fastener 64 is configured to extend initially through a second opening 24 in a retainer plate before passing through the second screw opening 58 in the spacer 50, thereby helping to secure the plate system 10 to the spacer 50. In other embodiments, the fasteners 62, 64 need not extend through the plate system 10, and need only extend through the spacer 50.

Adjacent the first screw opening 56 and the second screw opening 58 is a tool opening 57. In some embodiments, the tool opening 57 is threaded. The tool opening 57 can be configured to receive an insertion tool that is correspondingly threaded. The insertion tool can be used to deliver the spacer 50 to a surgical site prior to attaching the plate system 10 to the spacer 50.

In some embodiments, the spacer 50 is made at least in part of a natural material, such as allograft bone. In other embodiments, the spacer 50 is made at least in part of a non-natural material, such as PEEK. In some embodiments, the spacer 50 is sized and shaped to fit within a cervical disc space. In other embodiments, the spacer 50 is sized and shaped to fit within a thoracic or lumbar disc space.

FIGS. 5-8B show different views of a plate system 10 being used in conjunction with a pair of spacers 50a, 50b. In some embodiments, one or more methods can be performed in accordance with these figures, as will be discussed below.

FIG. 5 is a perspective view of one or more spacers inserted in between vertebrae in accordance with some embodiments. The first spacer 50a is positioned between a first vertebra 2 and a second vertebra 4, while the second spacer 50b is positioned between the second vertebra 4 and a third vertebra 6. As shown in FIG. 5, the trailing ends of the spacers 50a, 50b are exposed such that they are capable of receiving first and second screws through first screw opening 52 and second screw opening 54. Each of the spacers can be implanted via an insertion tool that is inserted through tool opening 57.

FIGS. 6A and 6B are different views of a base plate overlying the one or more spacers in FIG. 5 in accordance with some embodiments. The plate system 10 includes a base plate 20 having an upper portion 20a, a mid portion 20b and a lower portion 20c. Retainer plates have not yet been positioned above the base plate 20. Once the base plate 20 is delivered to the surgical site, the base plate 20 can be initially positioned relative to the spacers 50a, 50b. In some embodiments, a temporary fastener 42 (as shown in FIG. 7A) can be delivered to hold down the base plate 20. In some embodiments, the temporary fastener 42 can comprise a screw, nail or spike having a head portion and a shaft portion that is easily delivered and easily removed from bone. In some embodiments, the temporary fastener 42 can be a single spike. The use of the temporary fastener 42 is optional.

FIGS. 7A-7C are different views of the base plate and retainer plates overlying the one or more spacers in FIG. 5 in accordance with some embodiments. After the base plate 20 is positioned over the spacers 50a, 50b, one or more retainer plates 30a, 30b can be positioned over the base plate 20, as shown in FIG. 7A. The retainer plates 30a, 30b are each configured with holes or openings 32, 34 for receiving fasteners 44 therein. In some embodiments, the fasteners 44 comprise threaded screws having a head portion and a threaded shaft portion. In some embodiments, the fasteners 44 can be polyaxial. Once the retainer plates 30a, 30b are positioned over the base plate 20, the retainer plates 30a, 30b can be dynamically adjusted and angled. Fasteners 44 can then be received through the openings 32, 34 of the retainer plates 30a, 30b and into corresponding openings 56, 58 in a corresponding spacer 50a, 50b, thereby securing the retainer plates 20a, 20b (and thus the overall plate system 10) to the spacers 50a, 50b. Advantageously, when the retainer plates 30a, 30b are seated, the plates dynamically auto-correct into their final position as the fasteners 44 are inserted therein. By securing the plate system 10 to the one or more spacers 50a, 50b, this advantageously prevents inadvertent migration of the spacers, and also reduces the stress on the spacers and vertebrae. With the fasteners 44 positioned through the retainer plates 30a, 30b and into the spacers 50a, 50b, any optional temporary fasteners 42 can be removed.

Figure 8B:
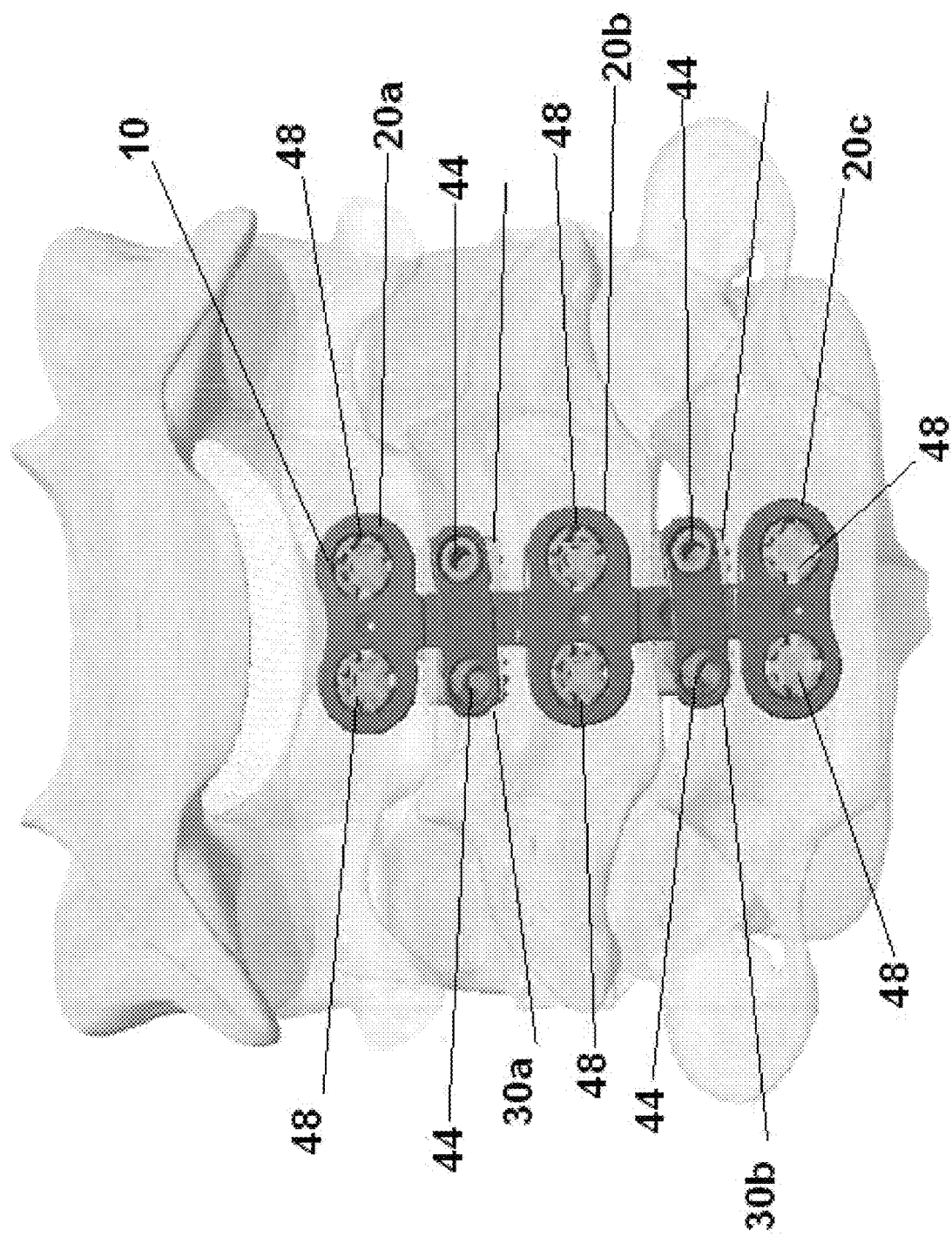

FIGS. 8A-8C are different views of the improved plate system 10 and associated spacers 50a, 50b in a final construct in accordance with some embodiments. With the temporary fasteners 42 removed from the base plate 20, non-temporary fasteners 48 can be inserted therein to secure the base plate 20 to adjacent vertebrae. In some embodiments, the fasteners 48 comprise screws having a head portion and a threaded shaft portion. In some embodiments, the fasteners 48 are polyaxial. Once the fasteners 48 are inserted into bone members, a final construct (as shown in FIGS. 8A-8C) is created. In some embodiments, the final construct comprises a base plate 20 attached to a first vertebra, a second vertebra and a third vertebra via fasteners 48; a first retainer plate 30a attached a first spacer 50a via fasteners 44; and a second retainer plate 30b attached to a second spacer 50b via fasteners 44. In some embodiments, a shorter base plate 20 (e.g., one that spans the length of two vertebrae) can be provided, while in other embodiments, a longer base plate 20 (e.g., one that spans the length of four or more vertebrae) can be provided. Likewise, in some embodiments, a single retainer plate 30 can be provided (e.g., to attach to a single spacer), while in other embodiments, more than two retainer plates (e.g., to attach to three or more spacers) can be provided.

FIGS. 9A-20 relate to embodiments of a plate system including one or more mechanisms that can be advanced to move (either by pushing or pulling) one or more spacers into a desirable location within a disc space. In some surgical procedures, implanted spacers may need to be pushed further into a disc space (e.g., more posteriorly). In order to push the spacers further, forceful tamping may need to be performed by a surgeon. Such forceful tamping may cause stress on both the vertebrae and on the spacers themselves (particularly on relatively fragile spacers comprised of allograft bone), that may result in inadvertent chipping and/or shearing of material within a patient. In some surgical procedures, implanted spacers may need to be brought closer to an anterior portion of the disc space, for which unnecessary force may also be used. The plate system embodiments shown in FIGS. 9A-20 are designed to alleviate the stress on the vertebrae and the spacers by providing mechanisms that provide controlled pushing or pulling of the spacers without the need for over forceful tamping.

FIGS. 9A and 9B are different views of an alternative improved plate system including a base plate and one or more push plates in accordance with some embodiments. The plate system 100 comprises a base plate 120 including an upper portion 120a, a mid portion 120b, and a lower portion 120c. The upper portion 120a includes a pair of holes or openings 122, 124 for receiving one or more fasteners therein for engaging a first vertebral body. The mid portion 120b includes a pair of holes or openings 126, 128 for receiving one or more fasteners therein for engaging a second vertebral body. The lower portion 120c includes a pair of holes or openings 130, 132 for receiving one or more fasteners therein for engaging a third vertebral body. A first bridge portion 125a is positioned between the upper portion 120a and the mid portion 120b, while a second bridge portion 125b is positioned between the mid portion 120b and the lower portion 125c. In some embodiments, the upper portion 120a, mid portion 120b and lower portion 120c are substantially flat such that an upper face is substantially or completely parallel to a lower face of the plate. In other embodiments, the upper portion 120a, mid portion 120b and lower portion 120c are at least partially curved. As shown in FIGS. 9A and 9B, in some embodiments, the entire perimeter of the base plate 120 can be curved and rounded without any edges. In other embodiments, only portions of the base plate 120 are curved and rounded without any edges.

As shown in FIGS. 9A and 9B, a pair of push plates 134, 136 are configured to be attached to the base plate 120. A first push plate 134 is operably attached to the first bridge portion 125a of the base plate 120. In some embodiments, the first push plate 134 can be threadingly received in a first threaded opening 129a formed in the first bridge portion 125a. Likewise, a second push plate 136 is operably attached to the second bridge portion 125b of the base plate 120. In some embodiments, the second push plate 136 can be threadingly received in a second threaded opening 129b formed in the second bridge portion 125b.

Each of the push plates 134, 136 are configured to have a contact surface for contacting a spacer body. First push plate 134 comprises a first contact surface 150, while second push plate 136 comprises a second contact surface 160. In some embodiments, the contact surfaces 150, 160 are flat. In other embodiments, the contact surfaces 150, 160 are curved. The contact surfaces 150, 160 are each designed to push into a corresponding spacer within a disc space, thereby moving the spacer into a more desirable position within the disc space. Furthermore, first push plate 134 comprises a first threaded post 154 surrounded by adjacent non-threaded posts 152, while second push plate 136 comprises a first threaded post 164 surrounded by adjacent non-threaded posts 162 (as shown in FIG. 10B). These features will be discussed further below.

In FIGS. 9A and 9B, the push plates 134, 136 are each in a first configuration whereby they reside adjacent or near the base plate 120. Upon actuation by an actuator (as shown in FIG. 10A), the push plates 134, 136 will be pushed outwardly away from the base plate 120 and into a second configuration (as shown in FIG. 10B). This allows the first contact surface 150 to controllably push on a first spacer and the second contact surface 160 to controllably push on a second spacer, thereby reducing the need to use forceful tamping on the spacers.

FIGS. 10A and 10B are different views of the improved plate system in FIGS. 9A and 9B with the push plates pushed outwardly from the base plate in accordance with some embodiments. As shown in FIG. 10A, each of the openings 129a, 129b are configured to receive an actuation member therein. First opening 129a is configured to receive first actuation member 144, while second opening 129b is configured to receive second actuation member 146. In some embodiments, the actuation members 144, 146 each comprise threaded actuating screws.

Rotation of the first actuation member 144 causes rotation of the first threaded post 154, thereby causing the first push plate 134 to extend outwardly away from the base plate 120. Likewise, rotation of the second actuation member 146 causes rotation of the second threaded post 164, thereby causing the second push plate 136 to extend outwardly away from the base plate 120. Advantageously, the actuation members 144, 146 each provide for controlled actuation of the push plates 134, 136, which in turn cause for controlled movement (e.g., translation) of corresponding spacers within their disc spaces.

FIGS. 11A-13B show different views of a plate system 100 being used in conjunction with a pair of spacers 50*a*, 50*b*. In some embodiments, one or more methods can be performed in accordance with these figures, as will be discussed below.

Figure 11A:
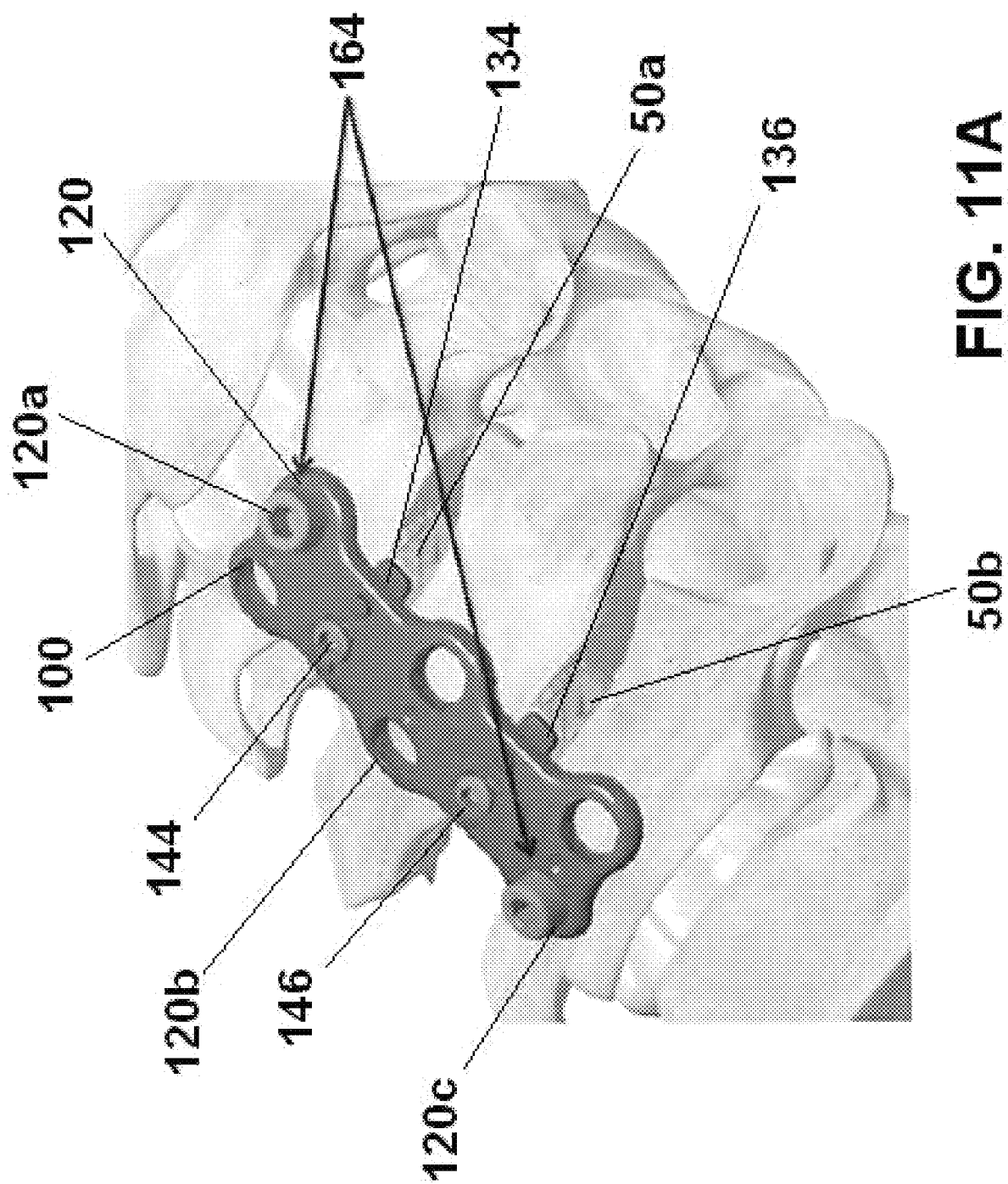
FIGS. 11A and 11B are different views of an improved plate system including push plates in a first configuration positioned over one or more spacers in accordance with some embodiments.
Figure 11B:
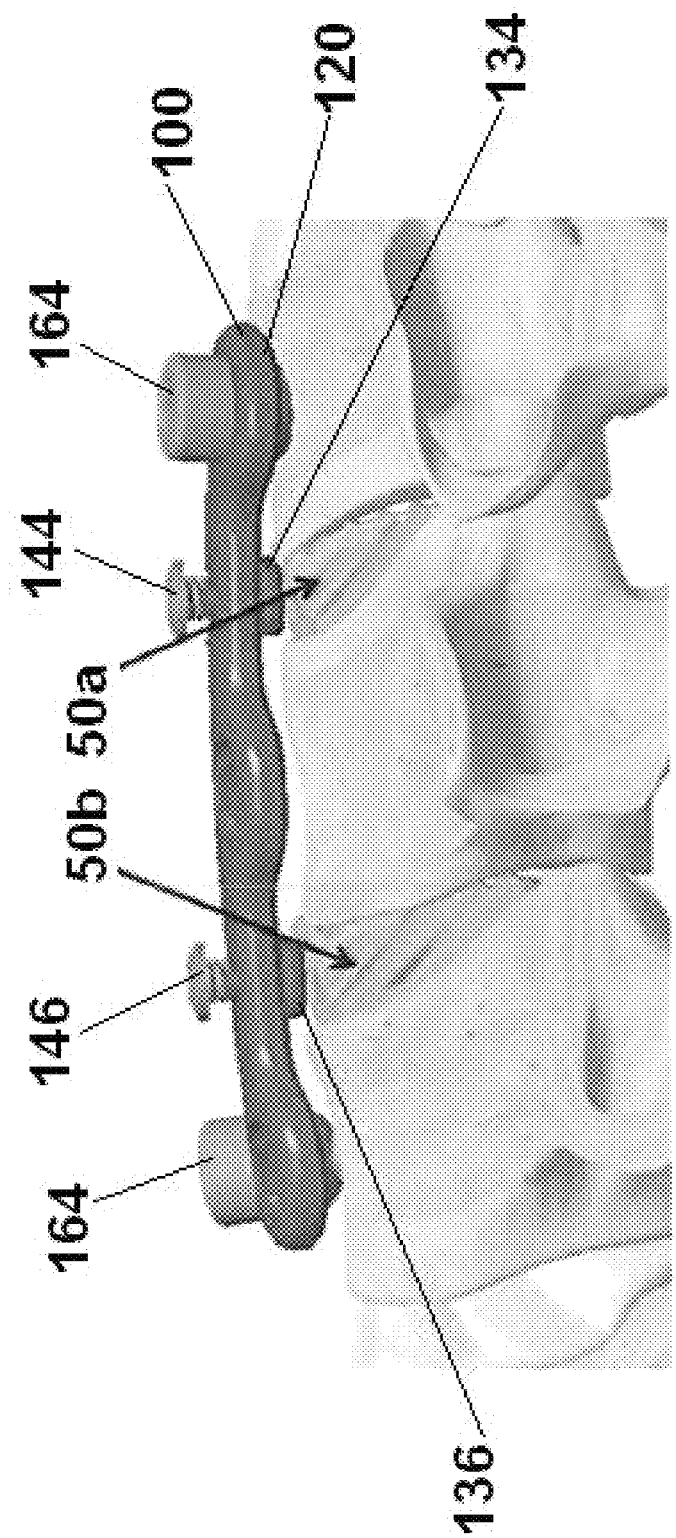

FIGS. 11A and 11B are different views of an improved plate system including push plates in a first configuration positioned over one or more spacers in accordance with some embodiments. As in FIG. 5, a pair of spacers 50*a* and 50*b* can be positioned between vertebrae. As shown in FIGS. 11A and 11B, a base plate 100 can be positioned on one or more vertebrae to reside over or overlay the spacers 50*a*, 50*b*. Optionally, one or more temporary fasteners (e.g., fixation screws) 164 can be inserted into the base plate 100 to maintain the base plate 100 in a desired orientation and position relative to the vertebrae before inserting non-temporary fasteners therein. The temporary fasteners can comprise a head portion and a threaded shaft portion, and can be in the form of a screw, nail or spike.

As shown in FIGS. 11A and 11B, first push plate 134 resides over the first spacer 50*a*, while second push plate 136 resides over the second spacer 50*b*. First push plate 134 can be actuated by actuation member 144, while second push plate 136 can be actuated by actuation member 146. In FIGS. 11A and 11B, the push plates 134, 136 are in a first configuration whereby they reside adjacent or closer to the base plate 120. In particular, FIG. 11B shows how actuation members 144, 146 have room to be downwardly threaded, such that the push plates 134, 136 can be pushed outwardly onto their corresponding spacers 50*a*, 50*b*.

Figure 12A:
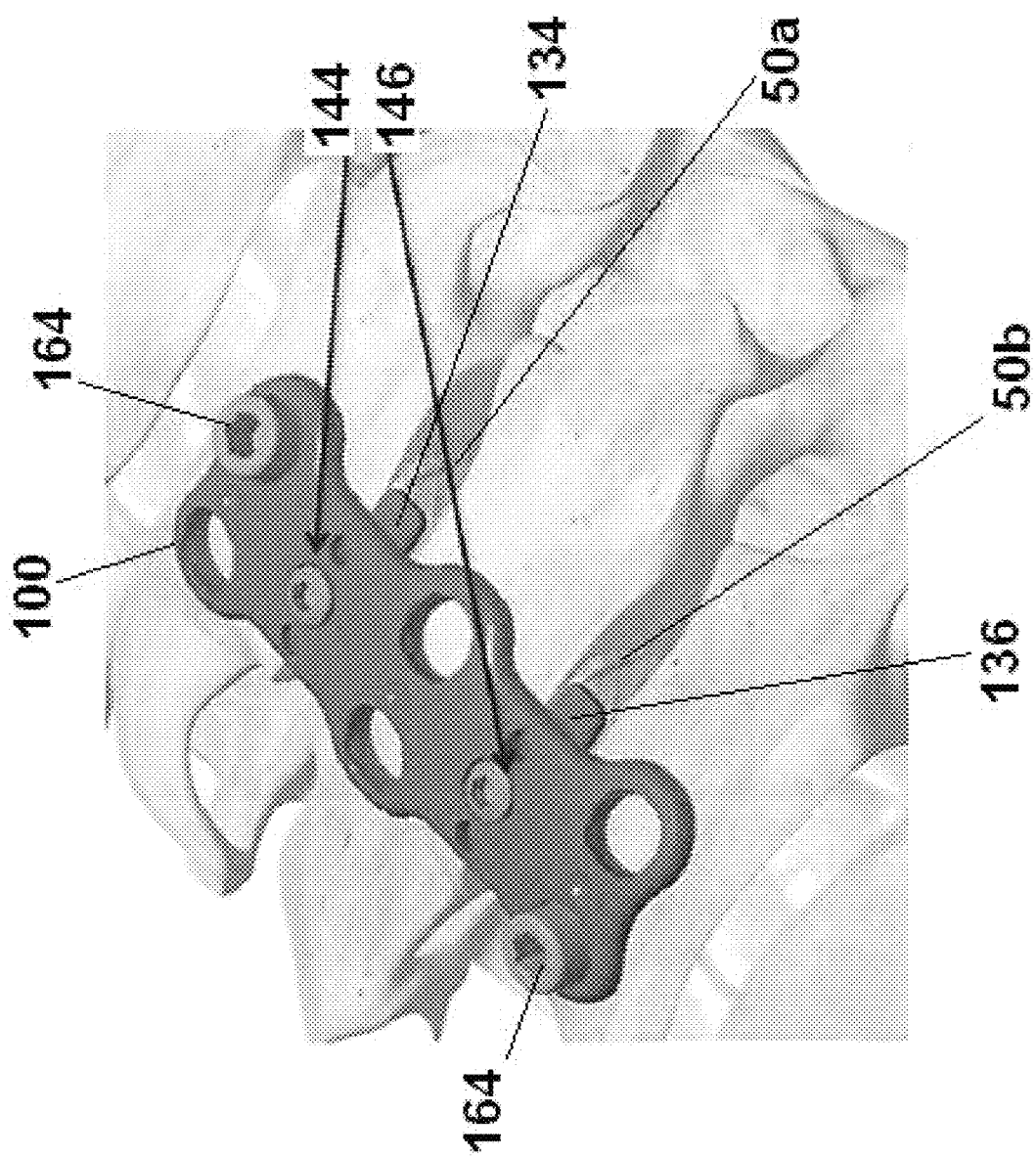

FIGS. 12A and 12B are different views of the improved plate system shown in FIGS. 11A and 11B with the push plates pushed outwardly to the spacers in a second configuration in accordance with some embodiments. In these figures, first actuation member 144 has been rotated such that the first push plate 134 is pushed outwardly from the base plate 120 into a second configuration, whereby it pushes into spacer 50*a*. Likewise, second actuation member 146 has been rotated such that second push plate 136 is pushed outwardly from the base plate 120 into a second configuration, whereby it pushes into spacer 50*b*. One skilled in the art will appreciate that the first push plate 134 need not be pushed the same distance as the second push plate 136, and in some embodiments, one push plate can be pushed outwardly while the other push plate remains closer to the base plate. In FIGS. 12A and 12B, however, both push plates 134, 136 are advantageously pushed outwardly such that they push their spacers 50*a*, 50*b* into a more desirable posterior location in a controlled fashion.

Once the spacers 50*a*, 50*b* have been pushed into a desired position, the push plates 134, 136 can each be returned to a position closer to their first configurations. In other words, each of the push plates 134, 136 can be brought closer to the base plate 120 via reverse rotation. At this point, the actuation members 144, 146 can be removed from the base plate 120 if desired. Furthermore, any temporary fasteners can also be removed and replaced with non-temporary or permanent fasteners.

Figure 13A:
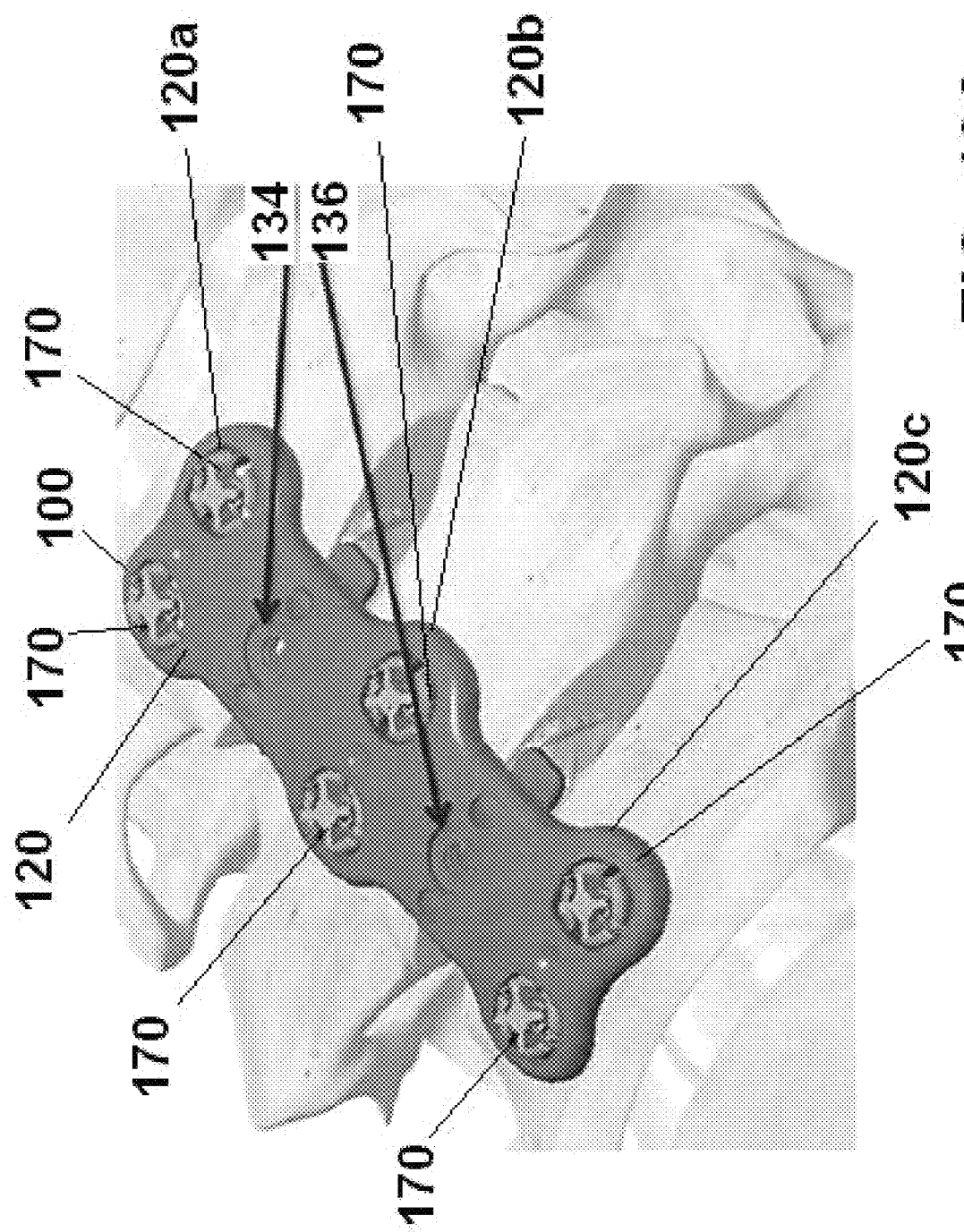
FIGS. 13A and 13B are different views of the improved plate system shown in FIGS. 11A and 11B in a final construct in accordance with some embodiments.
Figure 13B:
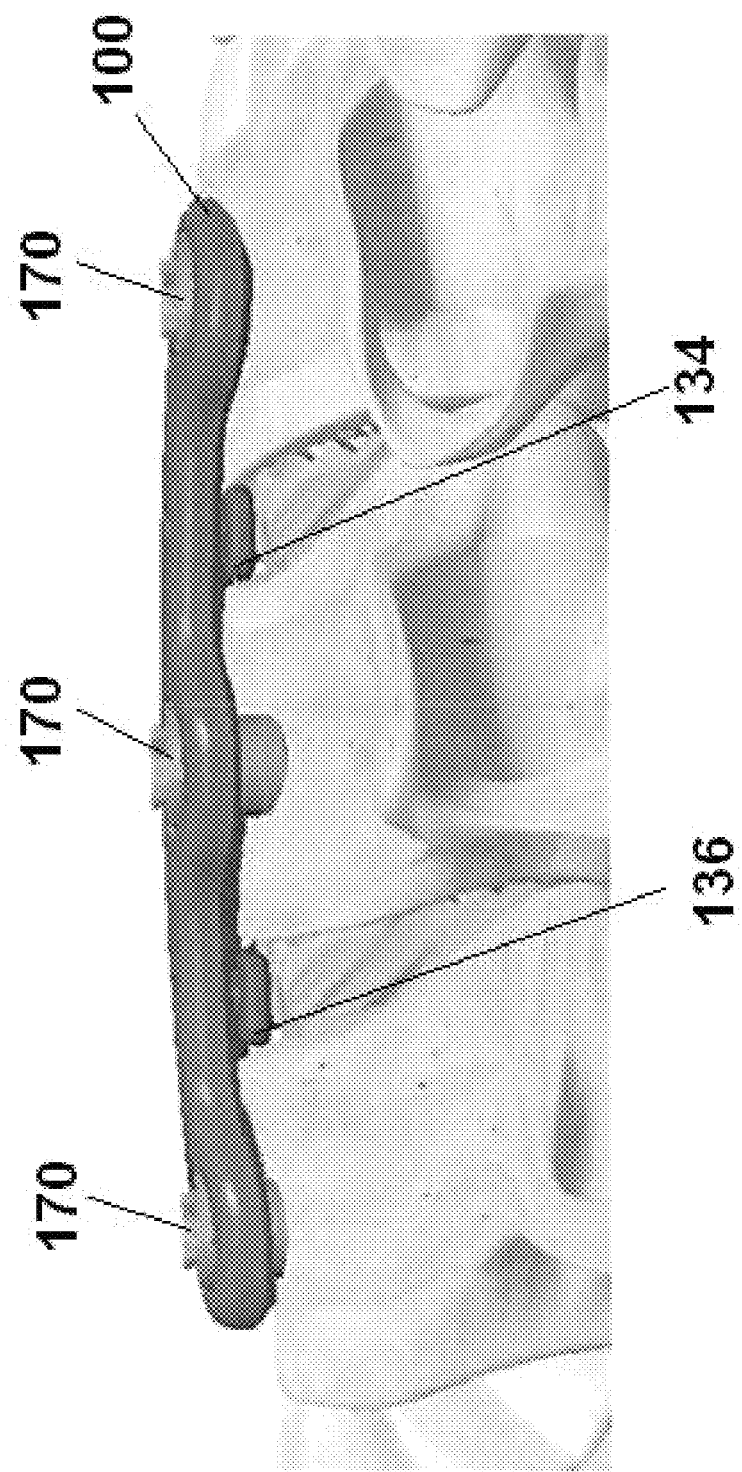

FIGS. 13A and 13B are different views of the improved plate system shown in FIGS. 11A and 11B in a final construct in accordance with some embodiments. In the final construct, non-temporary or permanent fasteners 170 have been inserted into the base plate 120 and into bone members. In the final construct, the upper portion 120*a* of the base plate 120 is attached to a first vertebral body, while the mid portion 120*b* is attached to a second vertebral body and the lower portion 120*c* is attached to a third vertebral body. As shown in FIG. 13A, the actuation members 144, 146 have been removed in the final construct. In other embodiments, the actuation members 144, 146 can be kept within the base plate 120 if desired. The base plate 120 advantageously provides stability as part of a spinal fusion procedure.

Figure 14:
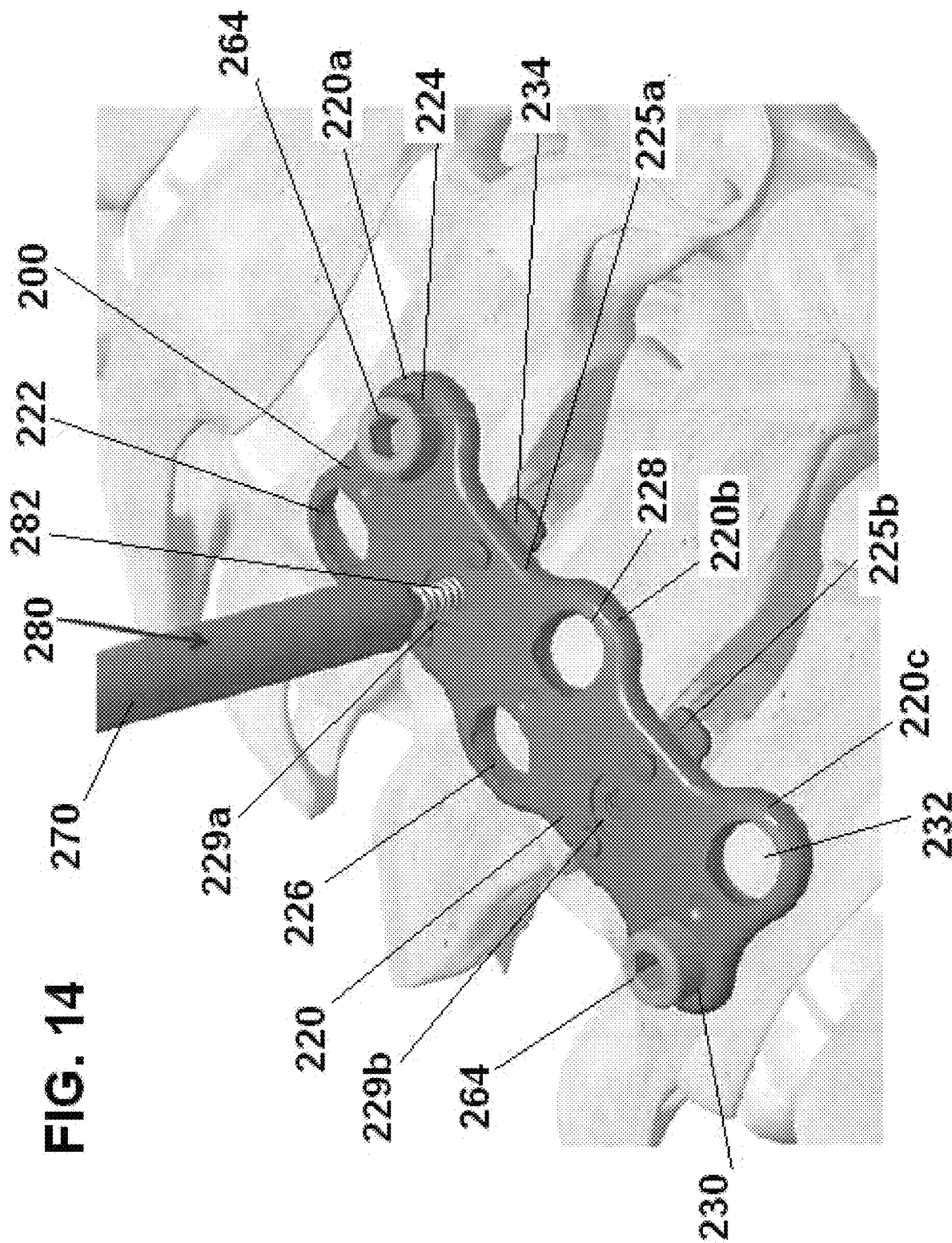
FIG. 14 is a perspective view of yet another alternative improved plate system including a base plate and one or more push plates actuated by a driver in accordance with some embodiments.

FIG. 14 is a perspective view of yet another alternative improved plate system including a base plate and one or more push plates actuated by a driver in accordance with some embodiments. Like the bone plate in FIG. 10A, the bone plate 200 comprises a base plate 220 including an upper portion 220*a*, a mid portion 220*b* and a lower portion 220*c*. The upper portion 220*a* comprises a pair of openings 222, 224 for receiving one or more fasteners therethrough for insertion into a first vertebra. The mid portion 220*b* comprises a pair of openings 226, 228 for receiving one or more fasteners therethrough for insertion into a second vertebra. The lower portion 220*c* comprises a pair of openings 230, 232 for receiving one or more fasteners therethrough for insertion into a third vertebra. The fasteners that are received in the openings can be temporary fasteners 262 (as shown in FIG. 14), or permanent. Furthermore, like the bone plate in FIG. 10A, the bone plate 200 includes a first push plate 234 and a second push plate 236 for advantageously pushing spacers into a more desirable position (e.g., more posteriorly) within their respective disc spaces.

In contrast to the embodiment in FIG. 10A which uses actuation members 144, 146 to actuate the push plates 234, 236, in the present embodiment, an instrument including a threaded driver can be used to actuate the push plates 234, 236. The instrument 270 can comprise an elongated shaft 280 having a distal threaded driver 282 attached thereto. In some embodiments, one or more instruments having a distal threaded driver 282 can be downwardly threaded into openings 229*a*, 229*b* formed in the base plate 220. Opening 229*a* is formed in bridge 225*a*, while opening 229*b* is formed in bridge 225*b*. As the distal threaded driver 282 is downwardly threaded into an opening 229*a*, 229*b*, the driver actuates a push plate 234, 236, thereby causing the push plate 234, 236 to push outwardly and into a spacer. This advantageously provides a controlled means to force a spacer into a more desirable (e.g., posterior) location, without the need for forceful tamping. Once one or more of the push plates 234, 236 have been used to push one or more spacers into a desired position, the distal threaded driver 282 can be reverse rotated, and the instrument 270 can be removed.

Figure 15B:
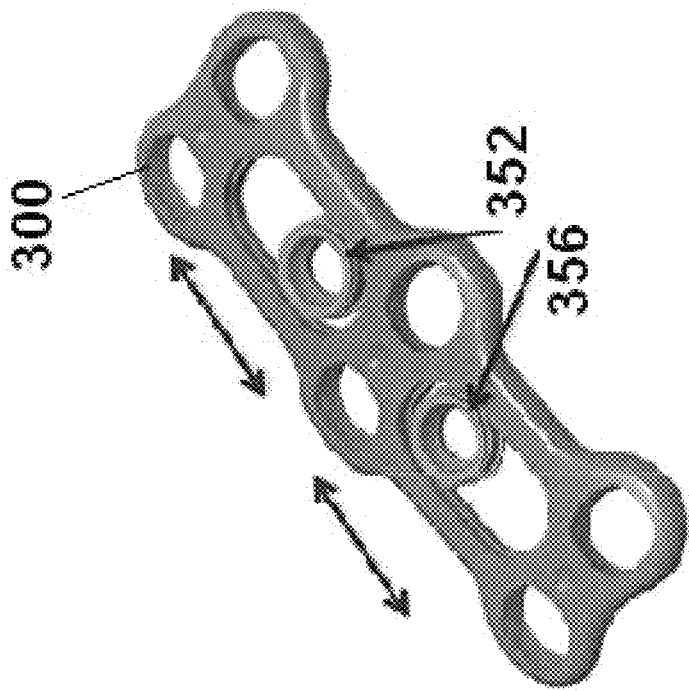
FIGS. 15A and 15B are different views of yet another alternative improved plate system including a translating boss in accordance with some embodiments.
Figure 15A:
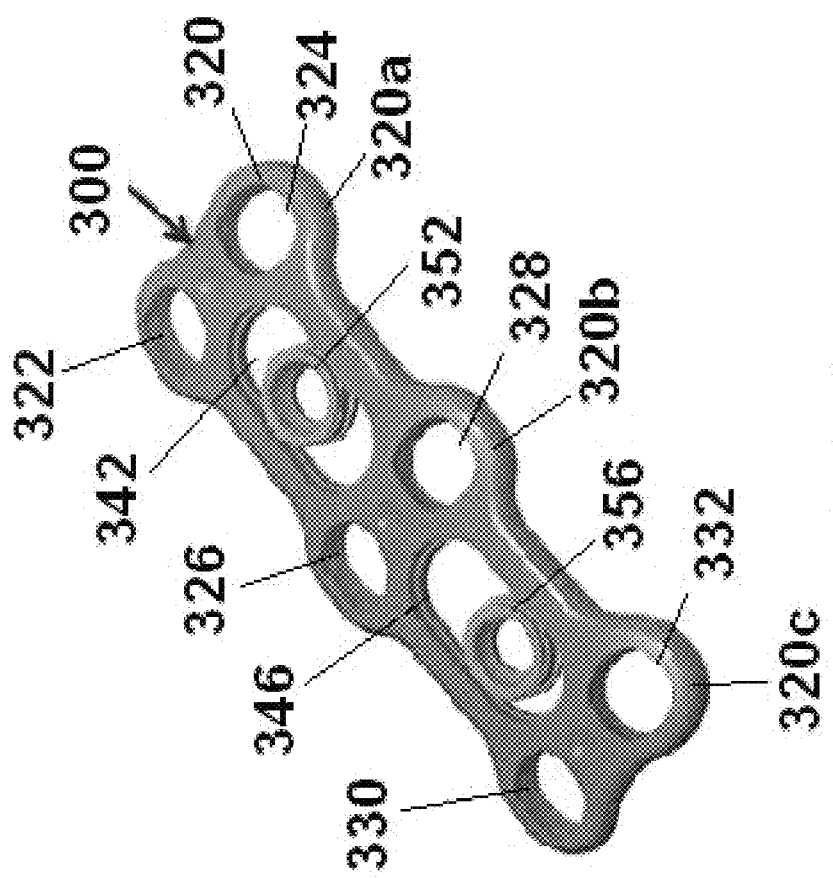

FIGS. 15A and 15B are different views of yet another alternative improved plate system including a translating boss in accordance with some embodiments. As in the prior embodiments in FIGS. 10A and 14, the plate system 300 provides one or more mechanisms for controllably moving one or more spacers into a desired position within a disc space. Advantageously, the one or more mechanisms include a translatable carriage or boss feature 352, 356 that receive a driver or screw 362, 366 (shown in FIGS. 16A and 16B) therein. By being translatable, a surgeon can move the boss 352, 356 such that it is over any portion of a spacer, thereby providing more options from which to move a spacer within a disc space.

The plate system 300 comprises a base plate 320 having a top portion 320*a*, a mid portion 320*b* and a lower portion 320*c*. The top portion 320*a* includes a pair of openings 322, 324 for receiving one or more fasteners therein for inserting into a first vertebra. The mid portion 320*b* includes a pair of openings 326, 328 for receiving one or more fasteners therein for inserting into a second vertebra. The lower portion 320c includes a pair of openings 330, 332 for receiving one or more fasteners therein for inserting into a third vertebra.

As shown in FIGS. 15A and 15B, the base plate 320 includes a first elongated opening 342 and a second elongated opening 346. The first elongated opening 342 is formed between the pair of openings 322, 324 in the top portion 320a and the pair of openings 326, 328 in the mid portion 320b of the base plate 320. The second elongated opening 346 is formed between the pair of openings 326, 328 in the mid portion 320b and the pair of openings 330, 332 in the lower portion 320c of the base plate 320. Each of the elongated openings 342, 346 is designed to receive a translatable carriage or boss 352, 356 therein. In some embodiments, each of the elongated openings 342, 346 comprises a track formed therein for receiving a translatable boss. In some embodiments, the track can be comprised of a recess (e.g., an inner recess for receiving a boss therein or an upper recess for which a boss can reside on top of). Advantageously, the first boss 352 is capable of translating along the first elongated opening 342 and the second boss 356 is capable of translating along the second elongated opening 346. By providing translation, the bosses 352, 356 are capable of being more accurately placed over corresponding spacers. Screws 352, 356 (shown in FIGS. 16A and 16B) placed through the bosses 352, 356 and into underlying spacers can be used to pull the spacers more anteriorly if desired in accordance with some embodiments.

Figures 16A, 16B:
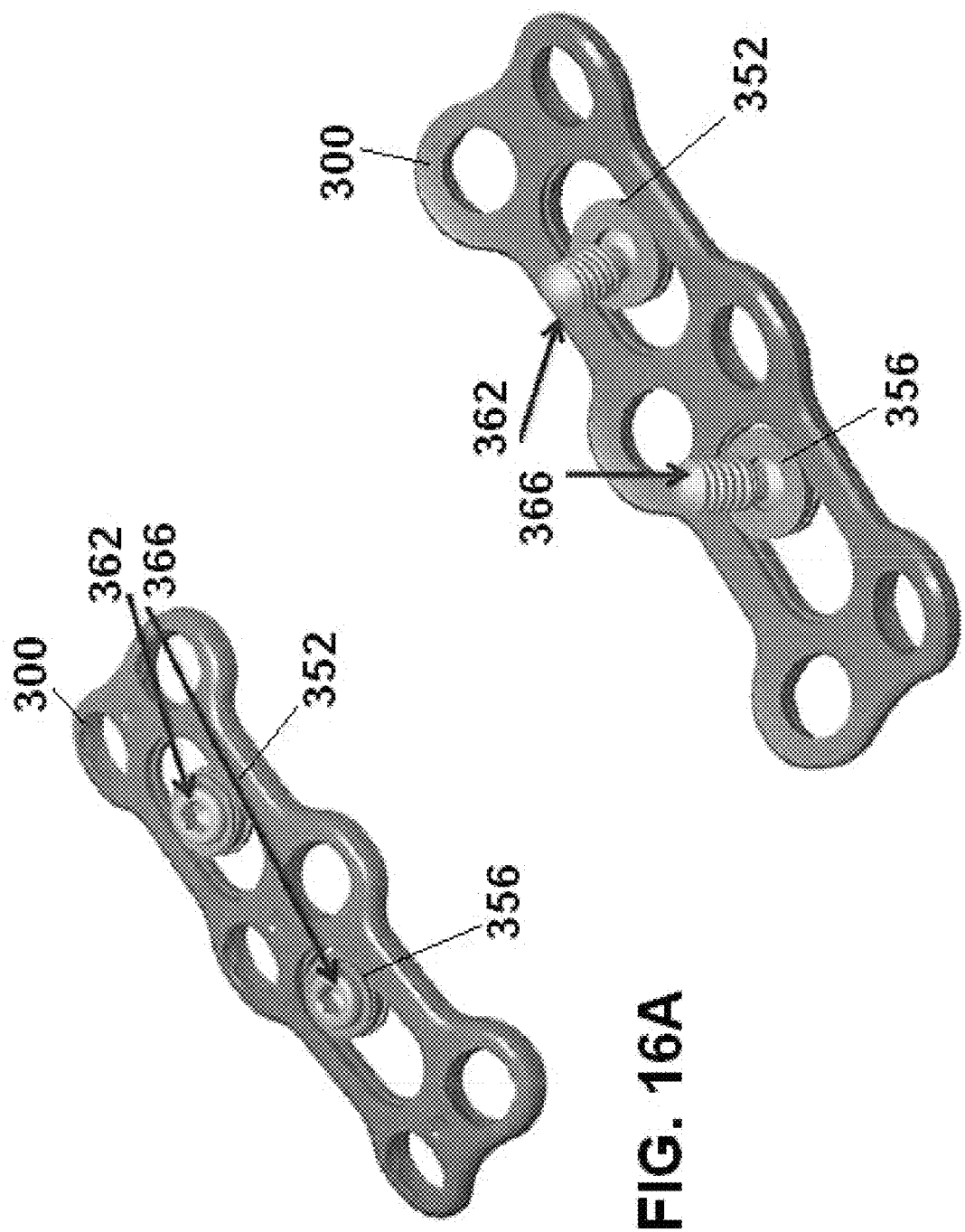
FIGS. 16A and 16B are different views of the improved plate system of FIGS. 15A and 15B with fasteners inserted therein.
Figure 20:
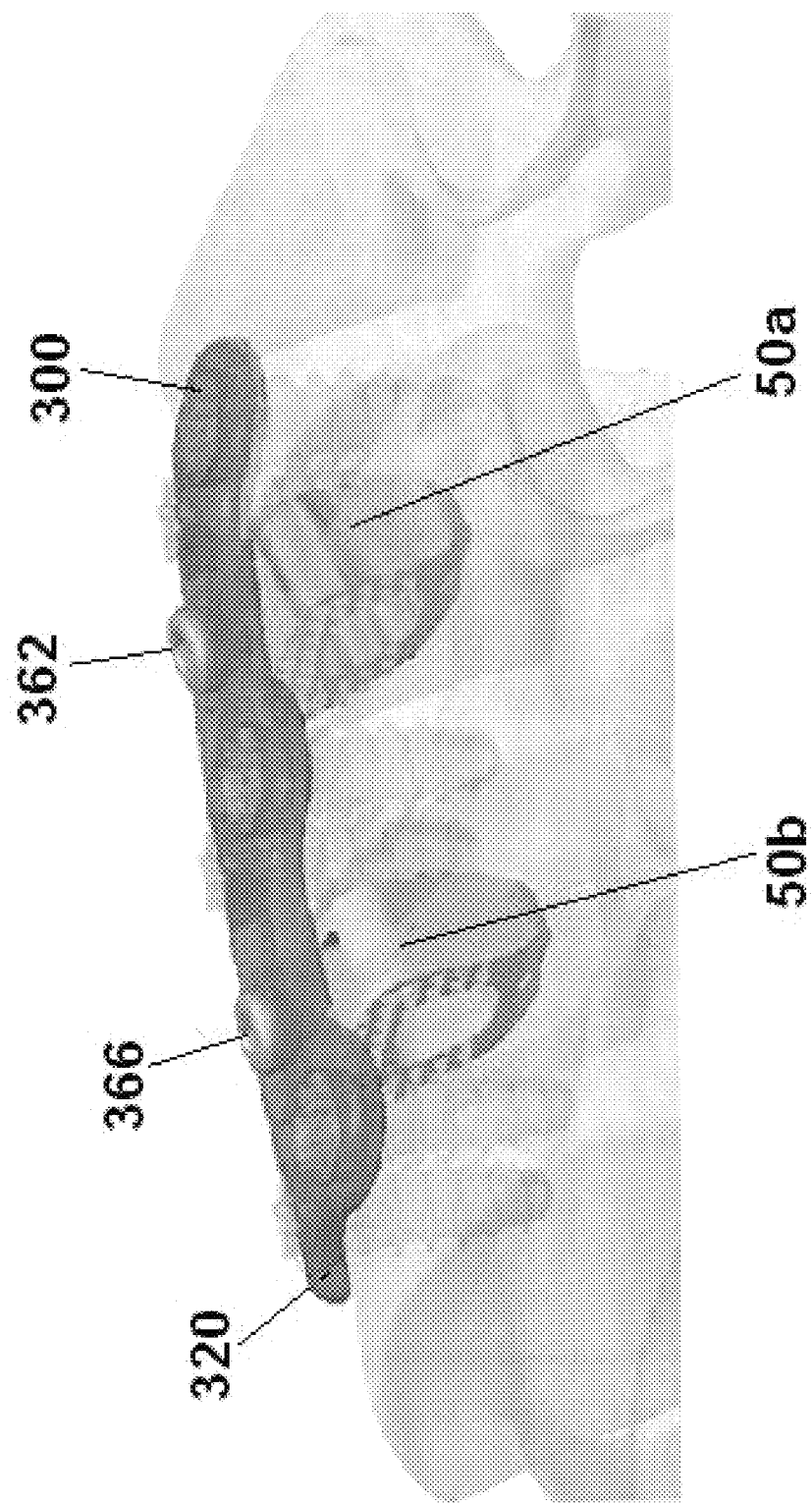
FIG. 20 is a view of the improved plate system of FIG. 18 in a final construct in accordance with some embodiments.

FIGS. 16A and 16B are different views of the improved plate system of FIGS. 15A and 15B with fasteners inserted therein. FIG. 16A shows a top perspective view of the plate system 300, while FIG. 16B shows a bottom perspective view of the plate system 300. In some embodiments, the translatable bosses 352, 356 can receive fasteners 362, 366 therethrough. In some embodiments, the fasteners 362, 366 can comprise screws (e.g., polyaxial screws) having a head portion and a threaded shaft portion. In the top view of FIG. 16A, the head portion of the screws 362, 366 are visible, while in the bottom view of FIG. 16B, the threaded shaft portion of the screws 362, 366 are visible. The threaded shaft portions of the screws 362, 366 are designed to engage spacer bodies, as shown in FIG. 20. In some embodiments, rotation of the screws 362, 366 results in the one or more spacers being brought closer to the base plate 300.

FIGS. 17-20 show different views of a plate system 300 being used in conjunction with a pair of spacers 50a, 50b. In some embodiments, one or more methods can be performed in accordance with these figures, as will be discussed below.

Figure 17:
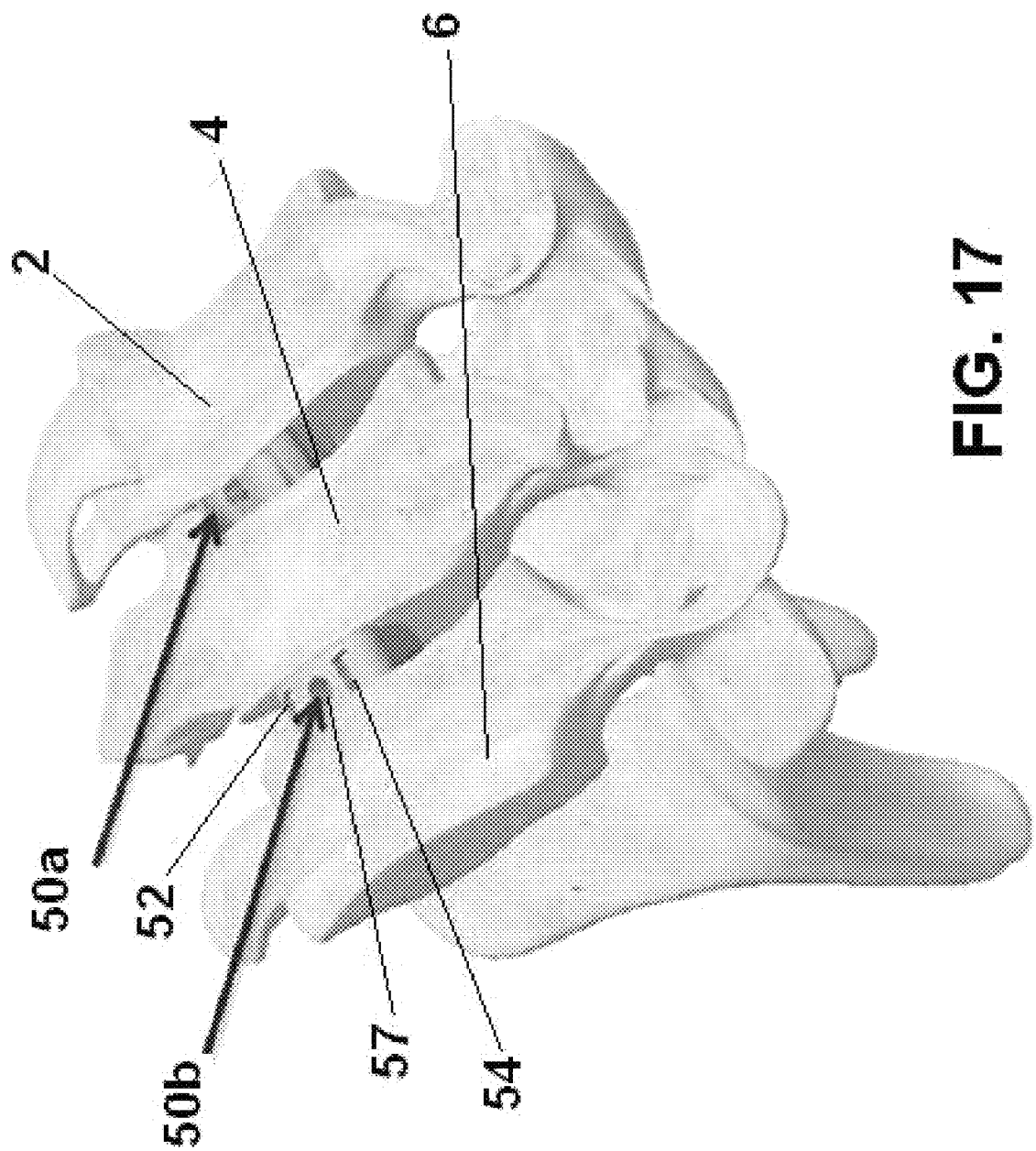
FIG. 17 is a perspective view of one or more spacers inserted in between vertebrae in accordance with some embodiments.

FIG. 17 is a perspective view of one or more spacers inserted in between vertebrae in accordance with some embodiments. The first spacer 50a is positioned between a first vertebra 2 and a second vertebra 4, while the second spacer 50b is positioned between the second vertebra 4 and a third vertebra 6. As shown in FIG. 17, the trailing ends of the spacers 50a, 50b are exposed such that they are capable of receiving first and second screws through first screw opening 52 and second screw opening 54. Each of the spacers can be implanted via an insertion tool that is inserted through tool opening 57.

Figure 18:
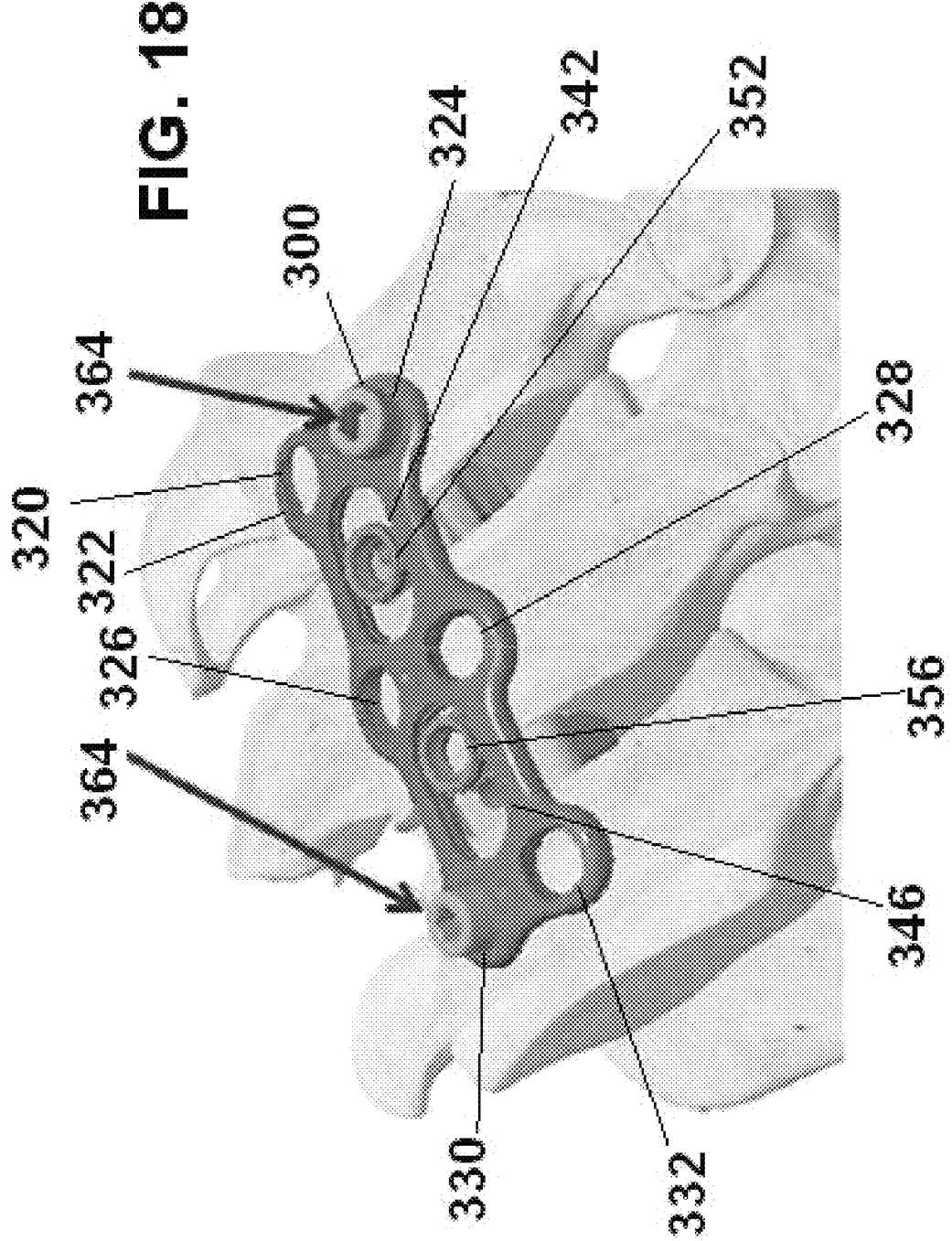
FIG. 18 is a perspective view of an improved plate system overlying the spacers in FIG. 17 with temporary screws placed therein in accordance with some embodiments.

FIG. 18 is a perspective view of an improved plate system overlying the spacers in FIG. 17 with temporary screws placed therein in accordance with some embodiments. The plate system 300 comprises a base plate 320 having an upper portion with openings 322, 324, a mid portion with openings 326, 328 and a lower portion with openings 330, 332. Fasteners, such as temporary fasteners 364, can be delivered through one or more of these openings and into bone, thereby holding the base plate 320 in place. As shown in FIG. 18, a first temporary fastener 364 is delivered into the first vertebra 2, while a second temporary fastener 364 is delivered into the third vertebra 6. At this point, translatable bosses 352, 356 that are received within elongated slots 342, 346 of the base plate 320 can be translated. Once the bosses 352, 356 are placed in a desired position above the spacers 50a, 50b, the plate system 300 is ready to receive one or more screws through the translatable bosses and into the spacers.

Figure 19:
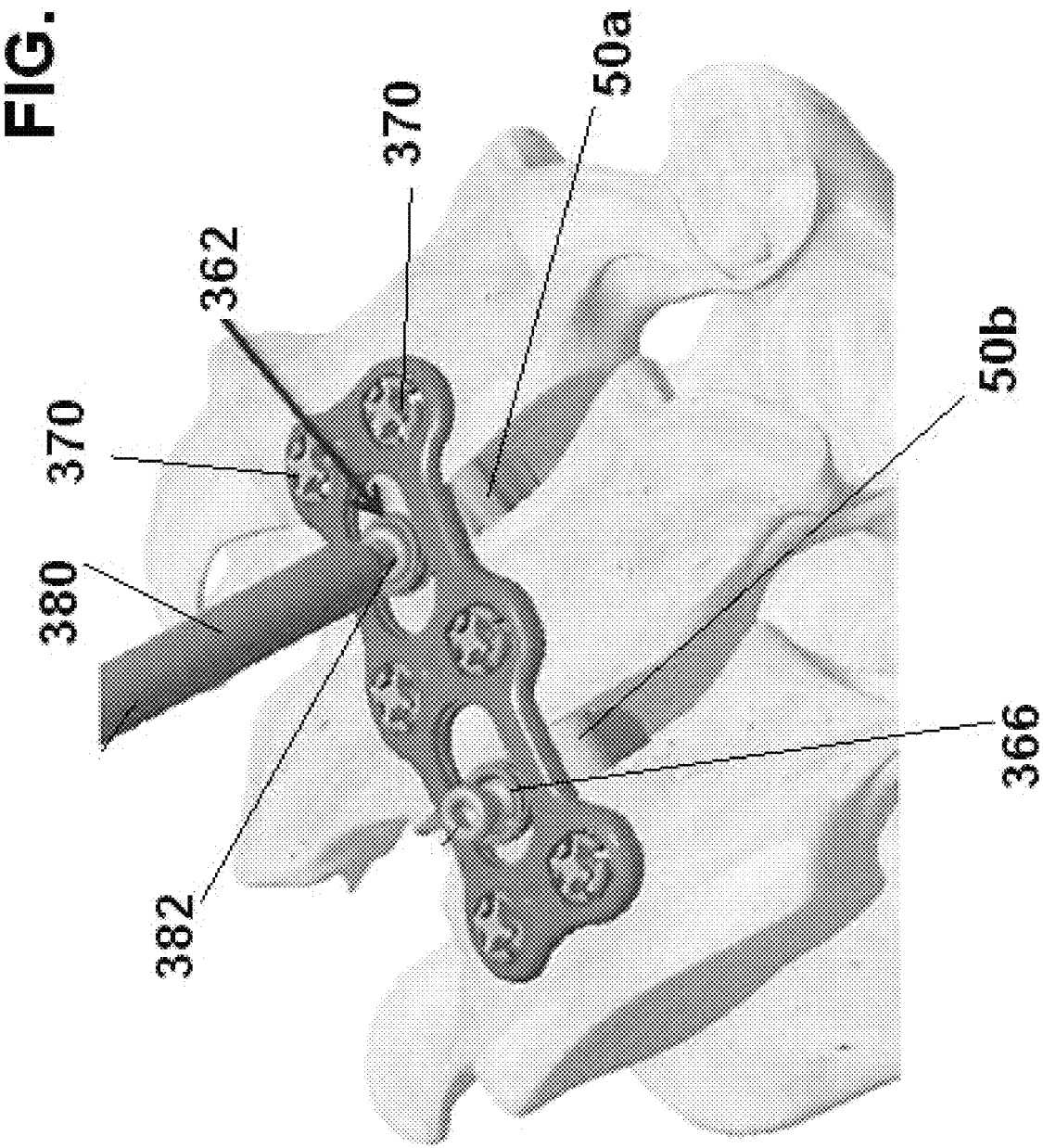
FIG. 19 is a perspective view of the improved plate system of FIG. 18 positioned over spacers and an instrument with a driver in accordance with some embodiments.

FIG. 19 is a perspective view of the improved plate system of FIG. 18 overlying spacers and an instrument with a driver in accordance with some embodiments. The instrument comprises an elongated shaft 380 and a threaded distal driver 382. The driver 382 is capable of driving first screw 362 and second screw 366 into engagement with the spacers 50a, 50b. As the driver 382 is rotated, each of the spacers 50a, 50b can be pulled upward toward the base plate 320, until the base plate 320 is adjacent or in close abutment with the base plate 320.

FIG. 20 is a view of the improved plate system of FIG. 18 in a final construct in accordance with some embodiments. As shown in this figure, each of the spacers 50a, 50b have been brought close to the base plate 320.

While the application herein disclosed has been described by means of specific embodiments and applications thereof, numerous modifications and variations can be made thereto by those skilled in the art without departing from the scope of the invention. It should be understood that variations and modifications within the spirit and scope of the invention might occur to those skilled in the art to which the invention pertains. Accordingly, all expedient modifications readily attainable by one versed in the art from the disclosure set forth herein that are within the scope and spirit of the present invention are to be included as further embodiments of the present invention.

What is claimed is:

1. An implantable plate system comprising:
   a base plate having an upper portion, a lower portion and a bridge positioned between the upper and lower portions, each of the upper and lower portions having a pair of fastener holes for receiving bone fasteners to engage with bone, the bridge having a pair of guide holes and an actuating hole disposed between the pair of guide holes;
   a push plate disposed under the base plate and having a pair of corresponding guide posts received in the guide holes of the bridge;
   wherein the push plate has a lower surface for contacting and pushing against a spacer implanted between two vertebral bodies;
   wherein the push plate is adapted to be pushed downwardly through the actuating hole
   wherein the push plate has a push post received in the actuating hole and the actuating hole is threaded such that a driver having a threaded tip pushes the push post to move the push plate away from the base plate.

2. The system of claim 1, further comprising an actuating threaded screw threadably received in the actuating hole and adapted to push the push plate.

3. The system of claim 1, wherein the push plate has a push post received in the actuating hole.

4. The system of claim 1, wherein the push plate has a threaded push post threadably received in the actuating hole.

5. An implantable plate system comprising:
a base plate having an upper portion, a lower portion and a bridge positioned between the upper and lower portions, each of the upper and lower portions having a pair of fastener holes for receiving bone fasteners to engage with bone, the bridge having a pair of guide holes and a threaded actuating hole disposed between the pair of guide holes;
a push plate disposed under the base plate and having a pair of corresponding guide posts slidably received in the guide holes of the bridge;
wherein the push plate has a lower surface for contacting and pushing against a spacer implanted between two vertebral bodies;
wherein the push plate is adapted to be pushed downwardly through the actuating hole,
wherein the push plate has a push post received in the actuating hole and when a driver having a threaded tip threadably received in the actuating hole rotates, the threaded tip pushes the push post downwardly.

6. The system of claim 5, further comprising an actuating threaded screw threadably received in the actuating hole and adapted to push the push plate downwardly when rotated.

7. The system of claim 6, wherein the push plate has a push post received in the actuating hole.

8. The system of claim 5, wherein each bone fastener is a polyaxial screw.

9. The system of claim 5, further comprising a pair of temporary fixation screws adapted to be received in the fastener holes to temporarily fix the base plate to the bone.

* * * * *